US007514221B2

(12) United States Patent
Breit et al.

(10) Patent No.: US 7,514,221 B2
(45) Date of Patent: Apr. 7, 2009

(54) DIAGNOSTIC ASSAY AND METHOD OF TREATMENT INVOLVING MACROPHAGE INHIBITORY CYTOKINE-1 (MIC-1)

(75) Inventors: Samuel Norbert Breit, Gordon (AU); David Alexand Brown, Bondi Beach (AU)

(73) Assignee: St. Vincent's Hospital Sydney Limited, Darlinghurst, New South Wales (AU)

( * ) Notice: Subject to any disclaimer, the term of this patent is extended or adjusted under 35 U.S.C. 154(b) by 0 days.

(21) Appl. No.: 10/257,597

(22) PCT Filed: Apr. 20, 2001

(86) PCT No.: PCT/AU01/00456

§ 371 (c)(1),
(2), (4) Date: May 23, 2003

(87) PCT Pub. No.: WO01/81928

PCT Pub. Date: Nov. 1, 2001

(65) Prior Publication Data

US 2004/0053325 A1    Mar. 18, 2004

(30) Foreign Application Priority Data

Apr. 20, 2000  (AU) .................................. PQ7037
May 11, 2000  (AU) .................................. PQ7465

(51) Int. Cl.
*G01N 33/53*  (2006.01)
(52) U.S. Cl. ...................... 435/7.1; 435/7.93; 530/388.8
(58) Field of Classification Search .................. 435/7.1, 435/6, 91.2
See application file for complete search history.

(56) References Cited

U.S. PATENT DOCUMENTS

| 5,994,102 | A | 11/1999 | Hudson et al. |
| 6,051,424 | A | 4/2000 | Kato et al. |
| 6,180,602 | B1 | 1/2001 | Kato et al. |
| 6,420,543 | B1 | 7/2002 | Lee et al. |
| 6,465,181 | B2 * | 10/2002 | Billing-Medel et al. ........ 435/6 |
| 6,500,638 | B2 | 12/2002 | Hudson et al. |
| 6,521,227 | B1 | 2/2003 | Hudson et al. |
| 2003/0059431 | A1 | 3/2003 | Hudson et al. |

FOREIGN PATENT DOCUMENTS

| JP | 250688 | 10/1995 |
| JP | 258293 | 10/1995 |
| WO | WO 96/18730 | 6/1996 |
| WO | WO 97/00958 | 1/1997 |
| WO | WO 99/06445 | 2/1999 |
| WO | WO 99/21011 | 4/1999 |
| WO | WO 00/70051 | 11/2000 |

OTHER PUBLICATIONS

Whisstock et al., "Prediction of protein function from protein sequence and structure" (2003) Quarterly Reviews of Biophysics, 36:307-340.*
Fairlie et al., "The propeptide of the transforming growth factor beta superfamily member, macrophage inhibitory cytokine-1 (MIC-1), is a multifunctional domain that can facilitate protein folding and secretion" (2001) j biol Chem 276:16911-16918.*
Li et al., J Biol Chem, 2000, 275:20127-20135.*
Fairlie et al. Biochemistry, 2001, 40:65-73.*
Harlow et al., Antibodies, A Laboratory Manual, 1988, Cold Spring Harbor laboratory, p. 76.*
Kuby, J. immunology, W.H. Freeman and Company, 1992, p. 125.*
Alberts et al., Molecular Biology of the Cell, 3$^{rd}$ edition, Garland publishing Inc, 1994, pp. 1255-1272.*
Yokoyama-Kobayashi, et al; "Human cDNA Encoding a Novel TGF-β Superfamily Protein Highly Expressed in Placenta"; J. Biochem., vol. 122, 622-626, (1997).
Lawton, et al; "Identification of a novel member of the TGF-beta superfamily highly expressed in human placenta"; Gene, vol. 203, 17-26; (1997).
Hillier, et al; "The Relationship of Amniotic Fluid Cytokines and Preterm Delivery, Amniotic Fluid Infection, Histologic Chorioamnionitis, and Chorioamnion Infection"; Obstetrics & Gynacology, vol. 81, 941-948; (1993).
Hromas et al; "PLAB, a novel placental bone morphogenetic protein"; Biochimica et Biophysica Acta, vol. 1354, 40-44; (1997).
Paralkar et al; "Cloning and Characterization of a Novel Member of the Transforming Growth Factor-β/Bone Morphogenetic Protein Family"; J. Biol. Chem., vol. 273, issue 22, 13760-13767; (1998).
Moore, et al; "The Transforming Growth Factor-β Superfamily Cytokine Macrophage Inhibitory Cytokine-1 Is Present in High Concentrations in the Serum of Pregnant Women"; The Journal of Clinical Endocrinology & Metabolism, vol. 85, No. 12, 4781-4788; (2000).
Fairlie, et al; "MIC-1 is a novel TGF-β superfamily cytokine associated with macrophage activation"; Journal of Leukocyte Biology, vol. 65, 2-5; (1999).
Bootcov, et al; "MIC-1, a novel macrophage inhibitory cytokine, is a divergent member of the TGF-β superfamily"; Proc. Nat'l. Acad. Sci USA, vol. 94, 11514-11519; (1997).
Strelau, et al; "GDF-15/MIC-1 a novel member of the TGF-β superfamily"; Journal of Neural Transmission; Supplementum 60; Advances in Research on Neurodegeneration vol. 8; 273-276; (2000).

(Continued)

*Primary Examiner*—Michael Szperka
(74) *Attorney, Agent, or Firm*—Nixon & Vanderhye

(57) ABSTRACT

Methods for diagnosing risk of miscarriage and/or premature birth. The method comprises (i) determining the amount of (MIC-1) present in a body sample taken from a pregnant test subject having a known gestation age and (ii) comparing the determined amount against the amount, or range of amounts, present in equivalent body sample(s) taken from normal pregnant subject(s) of a gestation age which is substantially equivalent to the known gestation age of the test subject.

10 Claims, 22 Drawing Sheets

OTHER PUBLICATIONS

Strelau, et al; "Growth/Differentiation Factor-15/Macrophage Inhibitory Cytokine-1 Is a Novel Trophic Factor for Midbrain Dopaminergic Neurons In Vivo"; The Journal of Neuroscience, vol. 20 (23), 8597-8603; (2000).

Bottner, et al; "Characterization of the rat, mouse, and human genes of growth/differentiation factor-15/macrophage inhibiting cytokine-1 (GDF-15/MIC-1)"; Gene, vol. 237, 105-111; (1999).

Bottner, et al; "Expression of a novel member of the TGF-β superfamily, growth/differentiation factor-15/macrophage-inhibiting cytokine-1 (GDF-15/MIC-1) in adult rat tissues"; Cell and Tissue Research, vol. 297, 103-111; (1999).

Bauskin, et al; "The propeptide of macrophage inhibitory cytokine (MIC-1), a TGF-β superfamily memer, acts as a quality control determinant for correctly folded MIC-1"; The EMBO Journal, vol. 19, No. 10, 2212-2220; (2000).

* cited by examiner

FIGURE 3A

Alignment of MIC-1 protein from cDNA clones bearing H6 or D6 Substitutions at position 202 of full length MIC-1 (position 6 of mature MIC-1)

```
                    10            20            30            40
  1  M P G Q E L R T L N G S Q M L L V L L V L S W L P H G G A L S L A E A S R A S P   MIC-1/D6
  1  M P G Q E L R T L N G S Q M L L V L L V L S W L P H G G A L S L A E A S R A S P   MIC-1/H6

50            60            70            80
 41  P G P S E L H D E D S R F R E L R K R Y E D L L T R L R A N Q S W E D S N T D L   MIC-1/D6
 41  P G P S E L H T E D S R F R E L R K R Y E D L L T R L R A N Q S W E D S N T D L   MIC-1/H6

90           100           110           120
 81  V P A V R I L T P E V R L G S G G H L H L R I S R A A L P E G L P E A S R L       MIC-1/D6
 81  V P A V R I L T P E V R L G S G G H L H L R I S R A A L P E G L P E A S R L       MIC-1/H6

130           140           150           160
121  H R A L F R L S P T A S R S W D V T R P L R R Q L S L A R P Q A P A L H L R L S   MIC-1/D6
121  H R A L F R L S P T A S R S W D V T R P L R R Q L S L A R P Q A P A L H L R L S   MIC-1/H6

170           180           190           200
161  P P P S Q S D Q L L A E S S S A R P Q L E L H L R P Q A A R G R R R A R A R N G   MIC-1/D6
161  P P P S Q S D Q L L A E S S S A R P Q L E L H L R P Q A A R G R R R A R A R N G   MIC-1/H6

210           220           230           240
201  D D C P L G P G R C C R L H T V R A S L E D L G W A D W V L S P R E V Q V T M C   MIC-1/D6
201  D H C P L G P G R C C R L H T V R A S L E D L G W A D W V L S P R E V Q V T M C   MIC-1/H6

Alignment of MIC-1 coding region DNA from cDNA clones bearing C to G substitution at position 604 ( H6 to D6 amino acid substitutions

```
                    10              20              30              40
  1  A T G C C C G G G C A A G A A C T C A G C A C G C T G A A T G G C T C T C A G A  MIC-1/H6
  1  A T G C C C G G G C A A G A A C T C A G G A C G C T G A A T G G C T C T C A G A  MIC-1/D6

50              60              70              80
 41  T G C T C C T G G T G T T G C T G G T G C T C T C G T G G C T G C C G C A T G G  MIC-1/H6
 41  T G C T C C T G G T G T T G C T G G T G C T C T C G T G G C T G C C G C A T G G  MIC-1/D6

90             100             110             120
 81  C G G C G C C C T G T C T C T G G C C G A G G C G A G C C G C G C A A G T T T C  MIC-1/H6
 81  C G G C G C C C T G T C T C T G G C C C A G G C G A G C C G C G C A A G T T T C  MIC-1/D6

130             140             150             160
121  C C G G G A C C C T C A G A G T T G C A C A C C G A A G A C T C C A G A T T C C  MIC-1/H6
121  C C G G G A C C C T C A G A G T T G C A C T C C G A A G A C T C C A G A T T C C  MIC-1/D6

170             180             190             200
161  G A G A G T T G C G C A A A C G C T A C G A G G A C C T G C T A A C C A G G C T  MIC-1/H6
161  G A G A C T T G C G G A A A C G C T A C G A G G A C C T G C T A A C C A G G C T  MIC-1/D6

210             220             230             240
201  G C G G G C C A A C C A G A G C T G G G A A G A T T C G A A C A C C G A C C T C  MIC-1/H6
201  G C G G G C C A A C C A G A G C T G G G A A G A T T C G A A C A C C G A C C T C  MIC-1/D6

250             260             270             280
241  G T C C C G G C C C C T G C A G T C C G G A T A C T C A C G C C A G A A G T G C  MIC-1/H6
241  G T C C C G G C C C C T G C A G T C C G G A T A C T C A C G C C A G A A G T G C  MIC-1/D6

290             300            -310             320
281  G G C T G G G A T C C G G C G G C C A C C T G C A C C T G C G T A T C T C T C G  MIC-1/H6
281  G G C T G G G A T C C G G C G G C C A C C T G C A C C T G C G T A T C T C T C G  MIC-1/D6

330             340             350             360
321  C G C C G C C C T T C C C G A G G G G C T C C C C G A G G C C T C C C G C C T T  MIC-1/H6
321  C C C C G C C C T T C C C G A G G G G C T C C C C G A G G C C T C G C G C C T T  MIC-1/D6

370             380             390             400
361  C A C C G G G C T C T G T T C C G G C T G T C C C C G A C G G C G T C A A G G T  MIC-1/H6
361  C A C C G G G C T C T G T T C C G G C T G T C C C C G A C G G C G T C A A G G T  MIC-1/D6

410             420             430             440
401  C G T G G G A C G T G A C A C G A C C T C T G C G G C G T C A G C T C A G C C T  MIC-1/H6
401  C G T G G G A C G T G A C A C G A C C G C T C T G G C G T C A G C T C A G C C T  MIC-1/D6

450             460             470             480
441  T G C A A G A C C C C A G G C G C C C G C G C T G C A C C T G C G A C T G T C G  MIC-1/H6
441  T G C A A G A C C C C A G G C G C C C G C G C T G C A C C T G C G A C T G T C G  MIC-1/D6

490             500             510             620
481  C C G C C G C C G T C G C A G T C G G A C C A A C T G C T G G C A G A A T C T T  MIC-1/H6
481  C C G C C G C C G T C G C A G T C G G A C C A A C T G C T G G C A G A A T C T T  MIC-1/D6
```

Decoration  Decoration #1   Shade (with solid block) residues that differ from MIC-1/H6

FIGURE 3B continued

```
              530              540              550              560
521  C G T C C G C A C G G C C C C A G C T G G A G T T G C A C T T G C G G C C G C A   MIC-1/H6
521  C G T C C G C A C G G C C C C A G C T G G A G T T G C A C T T G C G G C C G C A   MIC-1/D6

570              580              590              600
561  A G C C G C C A G G G G G C G C C G C A G A G C G C G T G C G C G C A A C G G G   MIC-1/H6
561  A G C C G C C A G G G G G C G C C G C A G A G C G C G T G C G C G C A A C G G G   MIC-1/D6

610              620              630              640
601  G A C C A C T G T C C G C T C G G G C C C G G C G T T G C T G C C G T C T G C     MIC-1/H6
601  G A C [G] A C T G T C C G C T C G G G C C C G G C G T T G C T G C C G T C T G C   MIC-1/D6

650              660              670              680
641  A C A C G G T C C G C G C G T C G C T G G A A G A C C T G G G C T G G G C C G A   MIC-1/H6
641  A C A C G G T C C G C G C G T C G C T G G A A G A C C T G G G C T G G G C C G A   MIC-1/D6

690              700              710              720
681  T T G G G T G C T G T C G C C A C G G G A G G T G C A A G T G A C C A T G T G C   MIC-1/H6
681  T T G G G T G C T G T C G C C A C G G G A G G T G C A A G T G A C C A T G T G C   MIC-1/D6

730              740              750              760
721  A T C G G C G C G T G C C C G A G C C A G T T C C G G G C G G C A A A C A T G C   MIC-1/H6
721  A T C G G C G C G T G C C C G A G C C A G T T C C G G G C G G C A A A C A T G C   MIC-1/D6

770              780              790              800
761  A C G C G C A G A T C A A G A C G A G C C T G C A C C G C C T G A A G C C C G A   MIC-1/H6
761  A C G C G C A G A T C A A G A C G A G C C T G C A C C G C C T G A A G C C C G A   MIC-1/D6

810              820              830              840
801  C A C G G T G C C A G C G C C C T G C T G C G T G C C C G C C A G C T A C A A T   MIC-1/H6
801  C A C G G T G C C A G C G C C C T G C T G C G T G C C C G C C A G C T A C A A T   MIC-1/D6

850              860              870              880
841  C C C A T G G T G C T C A T T C A A A A G A C C G A C A C C G G G G T G T C G C   MIC-1/H6
841  C C C A T G G T G C T C A T T C A A A A G A C C G A C A C C G G G G T G T C G C   MIC-1/D6

890              900              910              920
881  T C C A G A C C T A T G A T G A C T T G T T A G C C A A A G A C T G C C A C T G   MIC-1/H6
881  T C C A G A C C T A T G A T G A C T T G T T A G C C A A A G A C T G C C A C T G   MIC-1/D6

921  C A T A T G A     (SEQ ID NO: 3)                                   MIC-1/H6
921  C A T A T G A     (SEQ ID NO: 4)                                   MIC-1/D6
```

Decoration Decoration #1: Shade (with solid black) residues that differ from MIC-1/H6.

FIGURE 11
H6 restriction map
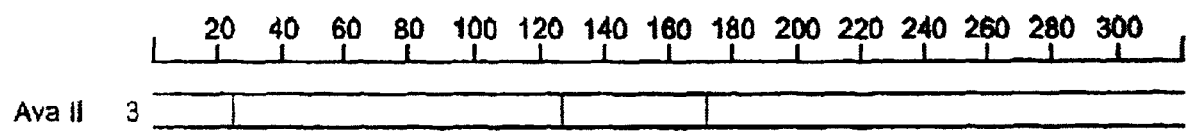
D6 restriction map
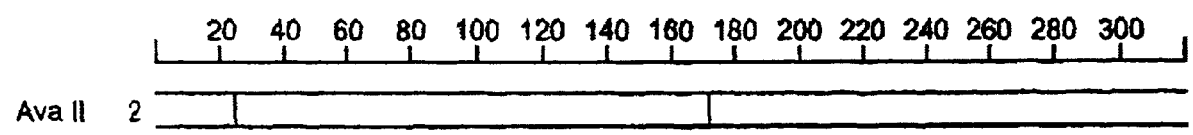

… # DIAGNOSTIC ASSAY AND METHOD OF TREATMENT INVOLVING MACROPHAGE INHIBITORY CYTOKINE-1 (MIC-1)

This application is a U.S. National Phase of PCT International Application No. PCT/AU01/00456 filed Apr. 20, 2001 which designated the U.S.

FIELD OF THE INVENTION

This invention relates to the field of medical diagnostics. In particular, the invention provides methods for diagnosing risk of miscarriage and/or premature birth, fetal abnormalities, cancer (e.g. prostate cancer) and inflammatory disease (e.g. rheumatoid arthritis). The invention also provides a method for reducing the risk of miscarriage and/or premature birth in pregnant subjects.

BACKGROUND TO THE INVENTION

The transforming growth factor-β (TGF-β) superfamily consists of an increasing number of molecules that regulate a variety of cellular processes such as growth, differentiation and oncogenesis. Members of the TGF-β superfamily have been classified into major family groupings which include TGF-β, bone morphogenic protein (BMP), growth and differentiation factor (GDF), inhibin/activin, mullerian inhibitory substance (MIS), glial derived neurotrophic factor (GDNF) and, more recently, macrophage inhibitory cytokine-1 (Bootcov et al., 1997). The involvement of the TGF-β superfamily in human pregnancy is indicated by the detection of TGF-β1, TGF-β2, TGF-β3, activin and inhibin in amniotic fluid and the localisation of TGF-β1, activin and inhibin to the placental villi (Graham et al., 1992; Petraglia et al., 1993a; Petraglia et al., 1992; Minami et al., 1992; Lang and Searle, 1994; Qu and Thomas, 1992; Altman et al., 1990; -Caniggia et al., 1999; Wallace et al., 1997).

The TGF-β superfamily has been studied intensively because of their biological importance and therapeutic potential. Their biology and functions are well known and have been extensively reviewed (e.g. Miyazono et al., 1993; Wahl, 1992; and Roberts et al., 1993). They are potent chemotactic factors for macrophages and fibroblasts and generally inhibit cell proliferation, perhaps because of their role in differentiation. In the context of inflammation, TGF-β is a potent stimulator of fibroblasts, collagen and matrix protein synthesis, promotes angiogenesis, modulates expression of adhesion molecules and inhibits lymphocyte proliferation, production of some lymphokines and NK cell function. TGF-β proteins have also been heavily implicated in the pathogenesis of chronic inflammatory processes and mechanisms.

The TGF-β superfamily is also thought to perform multiple roles during pregnancy. The ability of the TGF-β isoforms to modulate cell-cell adhesion, cell migration and tissue remodelling has led some authors to suggest that these molecules may control trophoblast invasion and implantation in early pregnancy. Other possible roles include regulation of fetal growth and suppression of the maternal immune system. Placental cells are a major source of TGF-β superfamily molecules and are regulated by at least TGF-β1, TGF-β3, activin and inhibin. For example, activin suppresses the production of inhibin and enhances progesterone, human chorionic gonadotropin (hCG), and gonadotropin-releasing hormone (GnRE) by placental cells (Petraglia et al., 1989). Inhibin suppresses placental hCG, GnRH and activin-induced progesterone release (Petraglia et al., 1989), while TGF-β1 suppresses placental derived human placental lactogen (hPL) production. Activin and TGF-β3 have also been shown to have opposing effects in regulating extravillous trophoblast invasion in early pregnancy (Caniggia et al., 1997; Caniggia et al., 1999). These findings suggest that TGF-β1, TGF-β3, activin and inhibin regulate the growth and differentiation of the placenta in an autocrine manner. TGF-β1, activin and inhibin are also present in the embryo proper where they have been demonstrated to regulate growth and differentiation. In particular, TGF-β superfamily members are well known for their ability to promote mesoderm induction.

It has also been suggested that TGF-β superfamily proteins promote foetal survival. Experimental evidence suggests that the amniotic fluid concentration of the pro-inflammatory cytolkines interleukin-1 (IL-1), IL-6, and tumour necrosis factor-α (TNF-α) rise during labour. Furthermore, pro-inflammatory cytokine production accompanying intrauterine infection has been associated with foetal rejection or preterm labour (Romero et al., 1992; Hillier et al., 1993; Opsjon et al., 1993). TGF-β1 and inhibin have been shown to suppress the production of pro-inflammatory cytolnes from macrophages and lymphocytes respectively (Bogdan and Nathan, 1993; Petraglia et al., 1991) while activin has pro-inflammatory effects on macrophages and amnion (Nusing and Barsig, 1997; Petraglia et al., 1993b). This has led to the suggestion that TGF-β1 and inhibin promote foetal survival by suppressing the production of pro-inflammatory cytokines by the maternal immune system.

The present applicants have recently cloned and characterised a divergent member of the TGF-β superfamily, macrophage inhibitory cytokine-1 (MIC-1) (Bootcov et al., 1997), whose expression is associated with macrophage activation. In order to determine the nature of any role MIC-1 may play in pregnancy, the present applicants have developed a sensitive sandwich enzyme-linked immunosorbent assay (ELISA) for MIC-1 quantification and used this to investigate the temporal relationship between human maternal serum MIC-1 concentrations and gestation age, and further, measured its concentration in amniotic fluid and placental extracts. In addition, the present applicants have conducted experimentation to delineate the origins of MIC-1 by assessing the capacity of a placental trophoblastic cell line (BeWo) to synthesise the cytokine. The results presented hereinafter shows that MIC-1 is able to promote fetal survival by suppressing the production of maternally-derived pro-inflammatory cytokines within the uterus. Consequently, quantitative diagnostic assays of MIC-1 in samples of maternal serum, amniotic fluid and placental extracts offers the possibility of detecting pregnant women with abnormal levels of MIC-1 and which are thereby at risk of miscarriage and/or premature birth.

In addition, the present applicants have found that a number of allelic variants of MIC-1 exist, all of which show minor amino acid sequence differences at positions 9, 48 and 202 (see International patent publication No. WO 97/00958, the entire contents of which is incorporated herein by reference, wherein MIC-1 is referred to as CL13). The most significant of these positions is amino acid position 202 since this corresponds to position 6 of the mature form of MIC-1 (i.e. with the leader sequence having been removed through cleavage). In some of the identified variants, the normal histidine (H) residue at position 202 (or "H6") is substituted with aspartic acid (D). This is due to a single nucleotide substitution within the MIC-1 gene such that a cytosine (C) at position 604 is substituted by a guanosine (G). The present applicants have now recognised that subjects which are either heterozygous or homozygous for the $Asp^{202}$-MIC-1 (or "D6") allelic variant may have an altered predisposition and disease course for inflammatory disease(s) and/or cancer(s).

DISCLOSURE OF THE INVENTION

Thus, in a first aspect, the present invention provides a method for the diagnosis or assessment of a disease or condition characterised by an abnormal level of expression of MIC-1, said method comprising;
(i) determining the amount of MIC-1 present in a body sample taken from a test subject, and
(ii) comparing said determined amount against the amount, or range of amounts, present in equivalent body sample(s) taken from normal subject(s).

Divergence between the compared amounts would indicate that the test subject has an abnormal level of MIC-1 expression which may be linked to a disease or condition. For instance, in a preferred embodiment of the invention, the detection of depressed MIC-1 amounts in a body sample, preferably a sample of blood serum, amniotic fluid or placental extracts, from a pregnant test subject would be indicative of a condition wherein there may be an increased risk of miscarriage and/or premature birth.

Thus, in a second aspect, the present invention provides a method for the diagnosis of miscarriage risk and/or premature birth, said method comprising;
(i) determining the amount of MIC-1 present in a body sample taken from a pregnant test subject having a known gestation age, and
(ii) comparing said determined amount against the amount, or range of amounts, present in equivalent body sample(s) taken from normal pregnant subject(s) of a gestation age which is substantially equivalent to said known gestation age of said test subject.

As mentioned above, preferred body samples for use in the method of the second aspect are samples of blood serum, amniotic fluid or placental extracts. However, samples of whole blood, plasma, urine and cerebrospinal fluid may also be suitable.

The amount, or range of amounts, present in body samples of normal pregnant subjects increases with advancing gestation age. It is therefore important that the determined amount of MIC-1 from the test subject sample be compared with the MIC-1 amount(s) present in equivalent sample(s) from normal pregnant subject(s) of substantially equivalent gestation age. Thus, where the body samples used are serum samples, a determined amount of less than or equal to 4 ng/ml from a first trimester test subject, less than or equal to 8 ng/ml from a second trimester test subject, and less than or equal to 12 ng/ml from a third trimester test subject, would be indicative of depressed MIC-1 levels and a consequent increased risk of miscarriage and/or premature birth. Where the body samples are amniotic fluid samples, a determined amount of less than or equal to 10 ng/ml from a second trimester test subject would be indicative of depressed MIC-1 levels and a consequent increased risk of miscarriage and/or premature birth. Finally, where the body samples used are placental extracts, a determined amount of less than or equal to about 18 ng/ml, more preferably less than or equal to about 10 ng/ml, in a placental extract sample of a third trimester test subject would be indicative of depressed MIC-1 levels and a consequent increased risk of miscarriage and/or premature birth.

Increased risk of miscarriage and/or premature birth may be the result of abnormal pregnancy and/or placental development associated-with depressed MIC-1 levels. That is, where abnormal placental development is determined through detection of depressed MIC-1 levels, this may be indicative of early induction of labour because the fetus may be at risk if the placenta fails to develop and grow normally.

Successfully assessing the risk of miscarriage and/or premature birth in pregnant women allows for the possibility of preventative therapies and other measures (e.g. rest, improved diet, etc.) to be applied.

The present invention also contemplates a method of treatment to reduce the risk of miscarriage and/or premature birth, involving the administration of MIC-1.

Thus, in a third aspect, the present invention provides a method of treating a pregnant subject to reduce the risk of miscarriage and/or premature birth, said method comprising administering to said subject an effective amount of MIC-1 optionally in admixture with a pharmacologically-acceptable carrier and/or excipient.

Preferably, the amount administered results in the total amount of MIC-1 (i.e. the amount of administered MIC-1 plus endogenous MIC-1) present in samples of placental extracts being maintained in the range of 15 to 70 ng/ml, more preferably 30 to 50 ng/ml.

MIC-1 may be administered by any of the commonly known routes, for example, orally, nasally, intravenously and intramuscularly. MIC-1 might also be administered directly to the uterus. The invention also contemplates the use of well known gene therapy techniques for MIC-1 administration, e.g. through the use of recombinant adenoviral or adenoviral-associated vectors including an expressible MIC-1-encoding nucleotide sequence, or through the use of linear MIC-1-encoding DNA operably linked to an appropriate promoter sequence and administered within liposomes.

The method of the third aspect may lead to the stimulation of placental growth and thereby overcome problems associated with abnormal placental development.

In another preferred embodiment of the invention, the detection of depressed or elevated MIC-1 amounts in a body sample from a pregnant test subject may be indicative of a condition wherein there may be an increased risk of fetal abnormalities.

Thus, in a fourth aspect, the present invention provides a method for the diagnosis of foetal abnormalities, said method comprising;
(i) determining the amount of MIC-1 present in a body sample taken from a pregnant test subject having a known gestation age, and
(ii) comparing said determined amount against the amount, or range of amounts, present in equivalent body sample(s) from normal pregnant subject(s) with a gestation age which is substantially equivalent to said known gestation age of said test subject.

The present applicants have also found that elevated MIC-1 expression is associated with cancers and the determination of the amount of MIC-1 from a suitable body sample(s) of a test subject would allow for the diagnosis (and monitoring of progression) of cancers, particularly prostate cancer, breast cancer, colonic cancer, rectal cancer and bladder cancer. For example, in serum samples from 50 subjects with either normal or elevated levels of prostate specific antigen (PSA; a marker of prostate cancer), a strong correlation was observed between MIC-1 and PSA and, in some patients, MIC-1 levels of greater than ten-fold above normal levels were determined (see FIG. 1). This strongly suggests that MIC-1 should be useful as a tumour marker and as a measure of progression in prostatic cancer. Further, observations of expression of MIC-1 in a wide range of epithelial cell types, indicates that MIC-1 may similarly be a useful tumour marker for cancers of the breast, colon, bladder and the like (see FIG. 19).

Thus, in a fifth aspect, the present invention provides a method for the diagnosis or assessment of a cancer characterised by an abnormal level of expression of MIC-1, said method comprising;
(i) determining the amount of MIC-1 present in a body sample taken from a test subject, and
(ii) comparing said determined amount against the amount, or range of amounts, present in equivalent body sample(s) from normal subject(s).

Preferably, the body sample used in the method of the fourth aspect is a sample of blood serum, plasma, urine, cerebrospinal fluid, synovial fluid, seminal fluid or tissue biopsy.

Further, the present applicants have found that elevated MIC-1 levels in certain body samples can be associated with rheumatoid arthritis. For example, examination of biopsies of subjects after treatment with a high dose of intravenously administered corticosteroid, showed a marked decrease in MIC-1 expression in infiltrating cells (see FIG. 2).

Thus, in a sixth aspect, the present invention provides a method for the diagnosis of rheumatoid arthritis, said method comprising;
(i) determining the amount of MIC-1 present in a body sample from a test subject, and
(ii) comparing said determined amount against the amount, or range of amounts, present in equivalent body sample(s) from normal subject(s).

The body sample used in the method of the sixth aspect may be a sample of urine, cerebrospinal fluid, seminal fluid or tissue biopsy. However, preferably, the body sample is a sample of blood serum or plasma, or synovial fluid.

The amount of MIC-1 present in a body sample may be readily determined by, for example, immunoassays or immunohistochemistry (e.g. with sections from tissue biopsies) using antibodies (monoclonal or polyclonal) or fragments thereof against MIC-1. Anti-MIC-1 antibodies and fragments thereof can be produced by any of the methods known to the art.

In a seventh aspect, the present invention provides a method of treating inflammation in a subject, said method comprising administering to said subject an effective amount of MIC-1 optionally in admixture with a pharmacologically-acceptable carrier and/or excipient.

In an eighth aspect, the present invention provides a method for the diagnosis or assessment of inflammatory disease and/or cancer in a human subject, said method comprising determining the presence of a MIC-1 variant protein having aspartic acid at position 202 or a position corresponding to position 202 of immature human wild type MIC-1 in a suitable sample from said subject.

In a ninth aspect, the present invention provides a method for assessing a predisposition to inflammatory disease and/or cancer in a human subject, said method comprising determining the presence of a MIC-1 variant protein having aspartic acid at position 202 or a position corresponding to position 202 of immature human wild type MIC-1 in a suitable sample from said subject.

Preferably, the inflammatory disease of the eighth and ninth aspects is rheumatoid arthritis. Preferably, the cancer of the eighth and ninth aspects is prostate cancer.

With regard to rheumatoid arthritis, detection of a MIC-1 variant protein having aspartic acid at position 202 or a position corresponding to position 202 of immature wild type human MIC-1 is indicative of rheumatoid arthritis or a predisposition to rheumatoid arthritis. With regard to prostate cancer, detection of a MIC-1 variant protein having aspartic acid at position 202 or a position corresponding to position 202 of immature wild type human MIC-1 may be indicative of an absence of prostate cancer or no or only a low predisposition to prostate cancer.

The presence of the variant MIC-1 protein may be readily determined by immunoassay using antibodies, or fragments thereof, capable of discriminating between normal human or "wild type" MIC-1 or variants which have histidine at position 202 and MIC-1 variants which have aspartic acid at position 202. Such antibodies, or fragments thereof, may be raised with MIC-1 or $Asp^{202}$-MIC-1 using any of the methods commonly known in the art. Alternatively, suitably discriminating antibodies, or fragments thereof, may be raised using immunogenic peptides, optionally conjugated to a carrier protein such as bovine serum albumin, which include an epitope spanning position 202 of immature human wild type MIC-1 protein or, in a variant protein, spanning a position corresponding to position 202 of immature human wild type MIC-1. For instance, an antibody which specifically binds to $Asp^{202}$-MIC-1 may be raised using an immunogenic peptide comprising the amino acid sequence; Ala-Arg-Asn-Gly-Asp-Asp-Cys-Pro-Leu (SEQ ID NO: 7).

Preferably, the presence of MIC-1 protein having aspartic acid at position 202 or a position corresponding to position 202 of immature human wild type MIC-1 is determined by immunoassay using an antibody which specifically binds to such a protein. However, where an antibody, or fragment thereof, is used which is specific for wild type MIC-1 and/or variants which have histidine at position 202 or a position corresponding to position 202 of immature human wild type MIC-1, the absence of any detectable binding, or a reduced level of binding, can be taken as being determinative of the presence of a MIC-1 variant protein having aspartic acid at position 202 or a position corresponding to position 202 of immature human wild type MIC-1. For such assays, it is preferred that a positive control be conducted to ensure the presence of a MIC-1 protein in the sample (e.g. by immunoassay with a non-discriminatory antibody, or fragment thereof, which binds to both wild type and variant MIC-1 proteins).

Preferred body samples for use in the method of the first and second aspect are samples of whole blood, serum, plasma and urine. Tissue biopsies may also be suitable.

It will be understood that subjects which are heterozygous or homozygous for a MIC-1 protein having the normal histidine at position 202 or a position corresponding to position 202 of immature human wild type MIC-1 may, conversely, show a reduced predisposition to inflammatory disease such as rheumatoid arthritis but an increased predisposition to cancer(s) such as prostate cancer.

Thus, in a tenth aspect, the present invention provides a method for the diagnosis or assessment of inflammatory disease and/or cancer in a human subject, said method comprising deter the presence of a MIC-1 variant protein having histidine at position 202 or a position corresponding to position 202 of immature human wild type MIC-1 in a suitable sample from said subject.

Assessment of inflammatory disease and/or cancer includes assessment of disease course. For example, it has been found that MIC-1 genotype and MIC-1 levels are predictive of cancer reappearance (e.g. after surgical removal) and mortality. That is, subjects which are homozygous for wild type MIC-1 (and/or variants which have histidine at position 202 or a position corresponding to position 202 of immature human wild type MIC-1), typically enjoy a longer duration to cancer reappearance (i.e. after treatment) than heterozygous subjects or subjects which are homozygous for $Asp^{202}$-MIC-1 variant. Further, it has been found that of the subjects homozygous for wild type MIC-1 (and/or variants which have histidine at position 202 or a position corresponding to position 202 of immature human wild type MIC-1), those with high levels of MIC-1 in a body sample (e.g. serum) show reduced survival times. Similarly, it has been found that of subjects suffering from rheumatoid arthritis, those which are heterozygous or homozygous for $Asp^{202}$-MIC-1 variant are likely to experience a worse degree of disease than subjects which are homozygous for wild type MIC-1 (and/or variants which have histidine at position 202 or a position corresponding to position 202 of immature human wild type MIC-1).

In an eleventh aspect, the present invention provides a method for assessing a predisposition to inflammatory disease and/or cancer in a human subject, said method comprising determining the presence of a MIC-1 variant protein having histidine at position 202 or a position corresponding to position 202 of immature human wild type MIC-1 in a suitable sample from said subject.

The invention further relates to methods for diagnosing and assessing a predisposition to inflammatory disease and/or cancer in a human subject involving genotyping (i.e. assessment of the allelic MIC-1 composition) of said subject. Such methods may utilise immunoassays involving discriminating anti-MIC-1 antibodies such as those described above, but may alternatively involve an assessment at the DNA level using polymerase chain reaction (PCR) analysis or any other appropriate technique for detecting single nucleotide differences between alleles (Chapter 7 of *Current Protocols in Human Genetics* Supplement 21, provides a review of a number of such techniques).

Thus, in a further aspect, the present invention provides a method for genotyping a human subject in relation to MIC-1, said method comprising determining whether said subject is homozygous or heterozygous for a MIC-1 protein having histidine at position 202 (e.g. wild type MIC-1) or a position corresponding to position 202 of immature human wild type MIC-1 or a MIC-1 variant protein which has aspartic acid at position 202 or a position corresponding to position 202 of immature human wild type MIC-1.

In a still further aspect, the present invention provides a method for diagnosing inflammatory disease and/or cancer in a human subject or, otherwise, assessing a predisposition to inflammatory disease-and/or cancer in a human subject, said method comprising genotyping said subject in relation to MIC-1 by determining whether said subject is homozygous or heterozygous for a MIC-1 protein having histidine at position 202 (e.g. wild type MIC-1) or a position corresponding to position 202 of immature human wild type MIC-1 or a MIC-1 variant protein which has aspartic acid at position 202 or a position corresponding to position 202 of immature human wild type MIC-1.

Subjects which are determined to be of homozygous D6/D6 genotype (i.e. wherein both MIC-1 alleles encode a MIC-1 variant protein having aspartic acid at a position corresponding to position 202 of immature human wild type MIC-1) and those which are determined to be of heterozygous H6/D6 genotype, may be expected to be suffering from, or show a predisposition to, inflammatory disease. Further, such subjects may be expected to be free of prostate cancer and/or show no or only a low predisposition to prostate cancer. Conversely, subjects determined to be of homozygous H6/H6 genotype may be expected to show an increased predisposition to prostate cancer.

Variant MIC-1 alleles may be conveniently determined by, for example, sequencing or restriction enzyme digest analysis of polymerase chain reaction (PCR) products obtained using DNA or RNA isolated from any suitable sample (e.g. a cheek cell sample) taken from the test individual. Alternatively, PCR may be conducted under high stringency conditions using primers targeted to the variable region of the MIC-1 encoding sequence to ensure that PCR products are only produced from the targeted wild type or variant MIC-1 sequence.

The DNA and amino acid sequences of human MIC-1 (i.e. "wild type") and the variant, $Asp^{202}$-MIC-1 are shown at FIG. 3.

As used herein, "immature human wild type MIC-1" refers to MIC-1 protein having the amino acid sequence shown in FIG. 3 as "MIC-1/H6", and "wild type MIC-1" refers to the mature form (i.e. with the leader sequence having been removed through cleavage) of that protein.

The terms "comprise", "comprises" and "comprising" as used throughout the specification are intended to refer to the inclusion of a stated step, component or feature or group of steps, components or features with or without the inclusion of a further step, component or feature or group of steps, components or features.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

The invention will hereinafter be described with reference to the following non-limiting examples and accompanying figures.

BRIEF DESCRIPTION OF THE ACCOMPANYING FIGURES

FIG. 1 provides a graph showing the relationship between serum MIC-1 and prostate specific antigen (PSA) levels from 50 subjects with elevated levels of PSA.

FIG. 2 provides a graph showing serum MIC-1 levels in 14 unselected subjects with rheumatoid arthritis.

FIG. 3 provides the amino acid sequences (A) and DNA sequences (B) of human MIC-1 and the variant, $Asp^{202}$-MIC-1.

FIG. 4 provides a graph showing the sensitivity of sheep and mouse anti-MIC-1 antisera. Plates were coated with 1.8 ng rhMIC-1, 2 ng rhTGF-β1, or coating buffer alone. Culture supernatant containing an anti-MIC-1 mouse monoclonal antibody (MAb), culture media conditioned by the mouse myeloma cell line SP2/0, unconditioned culture media DMEM+Nutridoma), and antibody diluant (Ab dil) were assessed undiluted while IgG enriched normal sheep serum and the sheep polyclonal antibody 233-P were diluted 1:500, 000 in Ab dil. Mouse IgG1 was assessed at 20 ng/ml.

FIG. 5 provides a recombinant human MIC-1 standard curve generated by sandwich ELISA utilising the anti-MIC-1 MAb for capture and the sheep polyclonal antibody 233B3-P for detection.

FIG. 6 provides the results of experimentation showing that MIC-1 is present in maternal serum and amniotic fluid during pregnancy in women. (A) Estimation of MIC-1 concentrations in pooled normal human serum (NHS), pooled staged maternal serum, and pooled amniotic fluid (AF) as determined by sandwich ELISA. (B) Immunoprecipitation and western blot analysis of MIC-1 in pooled normal human serum (lane 1), pooled staged maternal serum (lane 2-4), and pooled amniotic fluid (lane 5).

FIG. 7 gives the maternal serum MIC-1 concentrations in four pregnant women from 30 weeks of gestation until birth as determined by sandwich ELISA.

FIG. 8 gives the results of measurements of MIC-1 concentrations in five different human placental extracts as assessed by sandwich ELISA.

FIG. 9 provides the results of experimentation conducted to assess MIC-1 expression and secretion by the human trophoblastic cell line BeWo.

(A) MIC-1 secretion by BeWo cells after 1 and 5 days in culture as determined by sandwich ELISA.

(B) Immunoprecipitation and western blot analysis of secreted MIC-1 by BeWo cells. Lane 1, unconditioned culture media; Lane 2, culture media which had been conditioned by BeWo cells for 5 days.

(C) Reverse transcriptase-polymerase chain reaction (RT-PCR) analysis of MIC-1 expression by unstimulated BeWo cells. Lane 1, RT-PCR on total RNA from BeWo cells cultured for 24 h; Lane 2, Negative control (no total RNA); Lane 3, Positive PCR control.

FIG. 10 provides a typical standard curve from MIC-1 sandwich ELISA (rhMIC-1, 1000-7.8 pg/ml, i.e. 8 doubling dilutions).

FIG. 11 shows restriction enzyme cleavage points for AvaII in wild type MIC-1 and $Asp^{202}$-MIC-1 DNA sequences.

FIG. 12 shows a digest of a genomic PCR of six individuals labelled with indicated genotypes, confirmed by DNA sequencing. Run on 3% agarose gel with ethidium broxnide. The 45 base pair product of the PCR can be seen in the homozygote H6 marked by an arrow.

Figure 15:
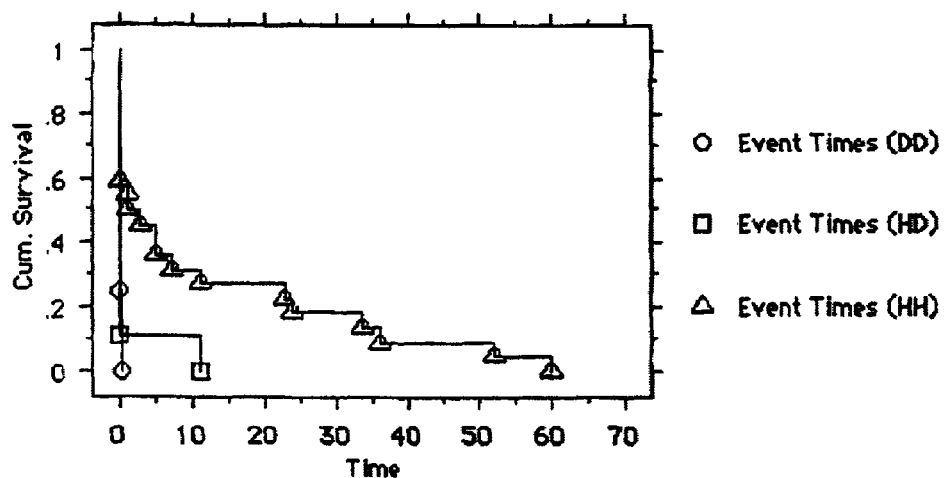

FIG. 15 provides a Kaplan-Meier plot for time to relapse from diagnosis in patients who died of colorectal carcinoma. Time is measured in months.

Figure 16:
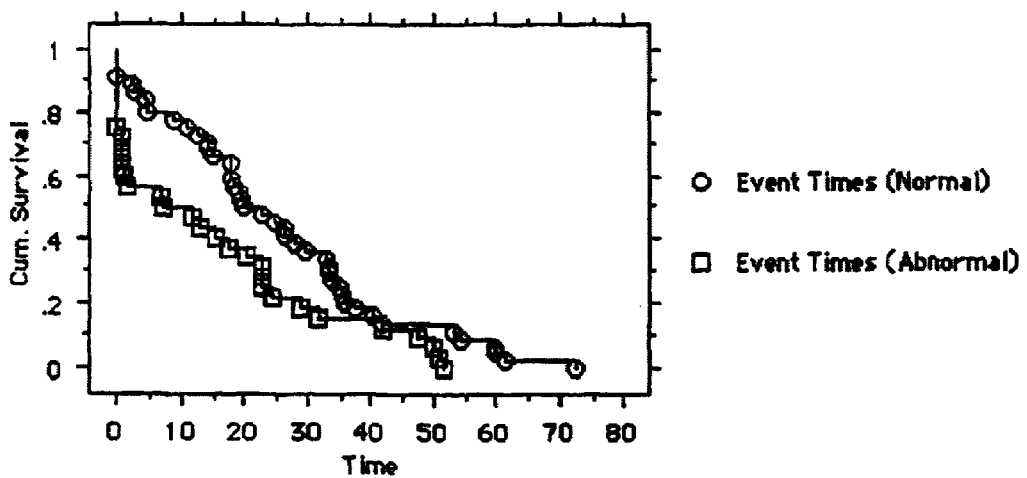

FIG. 16 provides a Kaplan-Meier plot for time to relapse from diagnosis in homozygous H6/H6 patients. Time measured in months.

Figure 17:
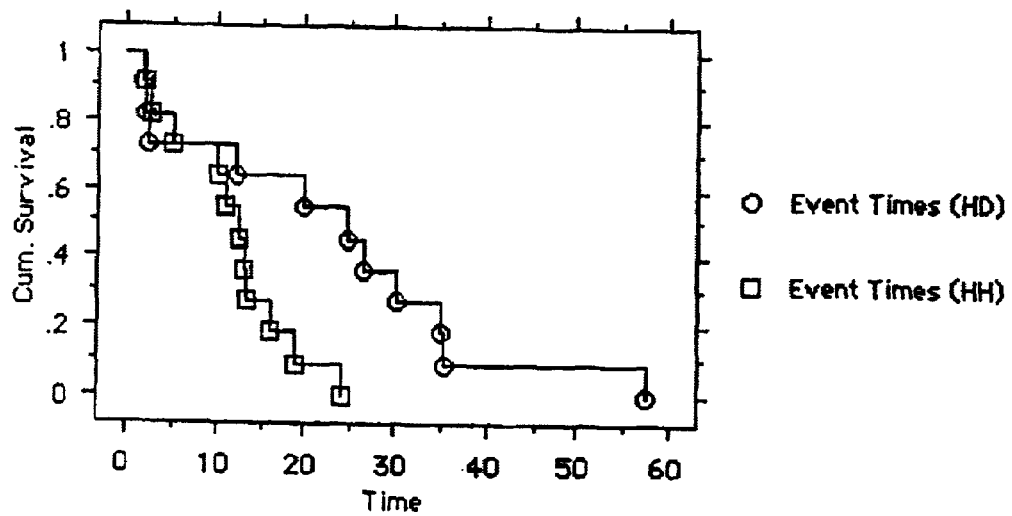

FIG. 17 provides a Kaplan-Meier plot for time to death from diagnosis in Dukes D CRC. Time measured in months.

Figure 18:
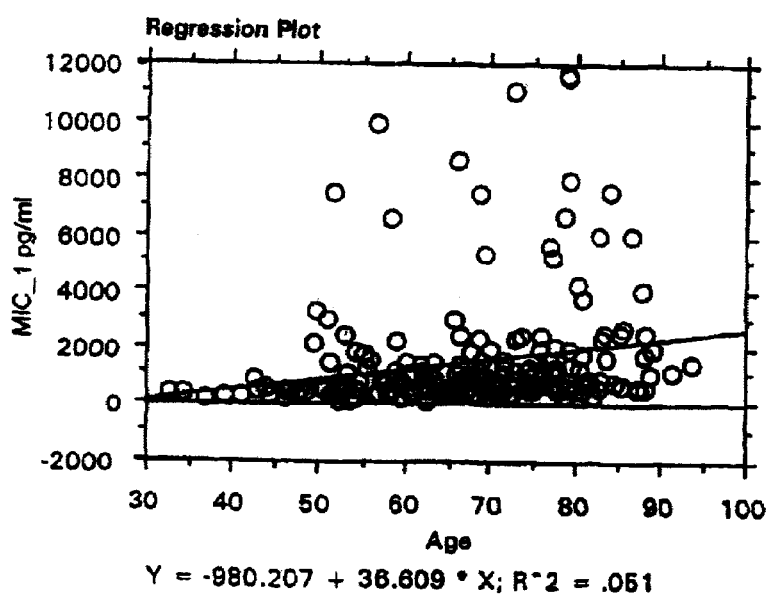

FIG. 18 provides a simple regression plot of MIC-1 related to age.

Figure 19:
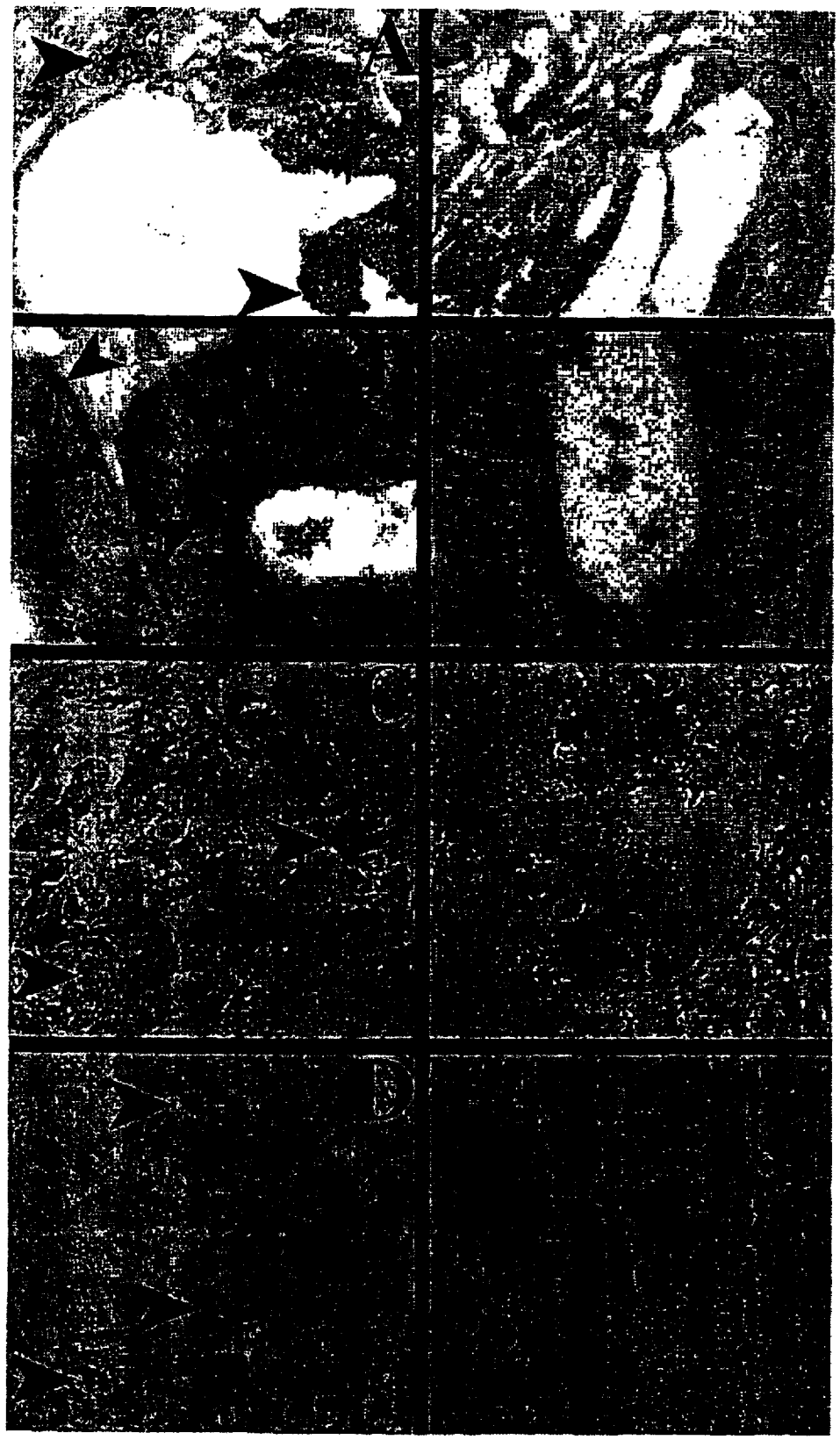

FIG. 19 shows immunohistochemistry for MIC-1 with 233-P. A. Prostate carcinoma; B. Bowel carcinoma; C. Breast carcinoma; D. Rheumatoid synovium. Arrows represent areas of MIC-1 stain. Panels on right are the respective controls stained with IgG enriched normal sheep serum.

Figure 20:
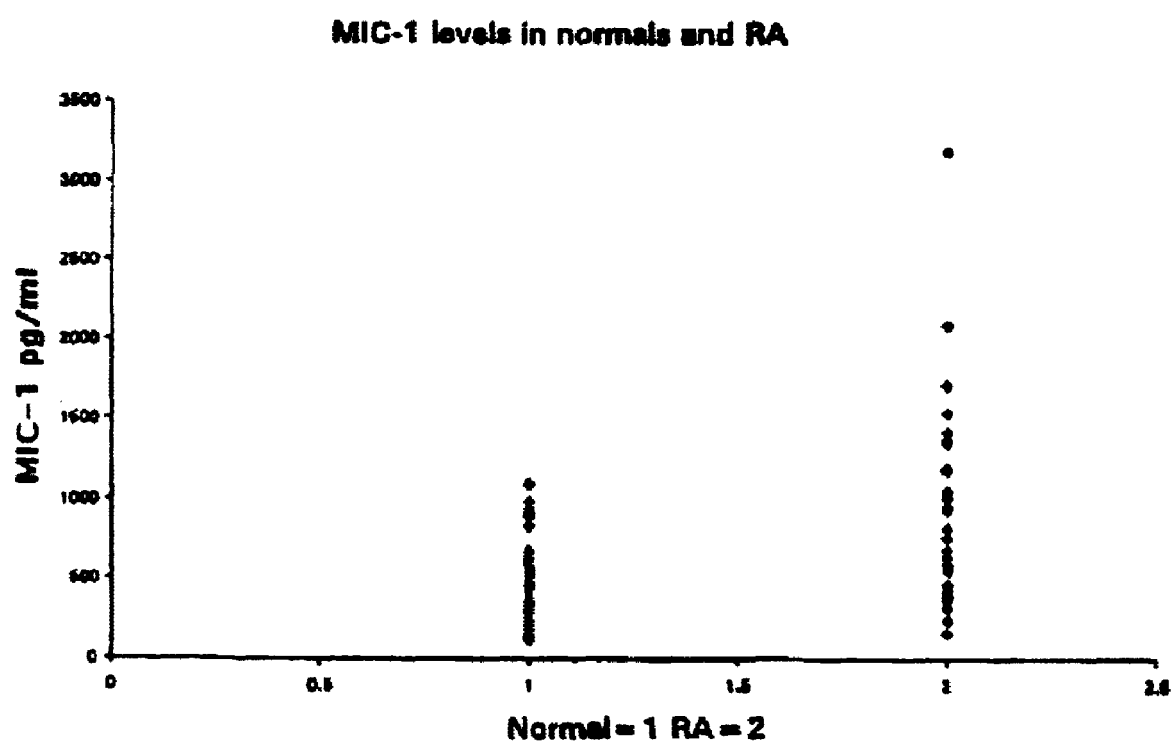

FIG. 20 shows MIC-1 levels in normal subjects compared with RA patients, as measured by MIC-1 sandwich ELISA.

Figure 21:
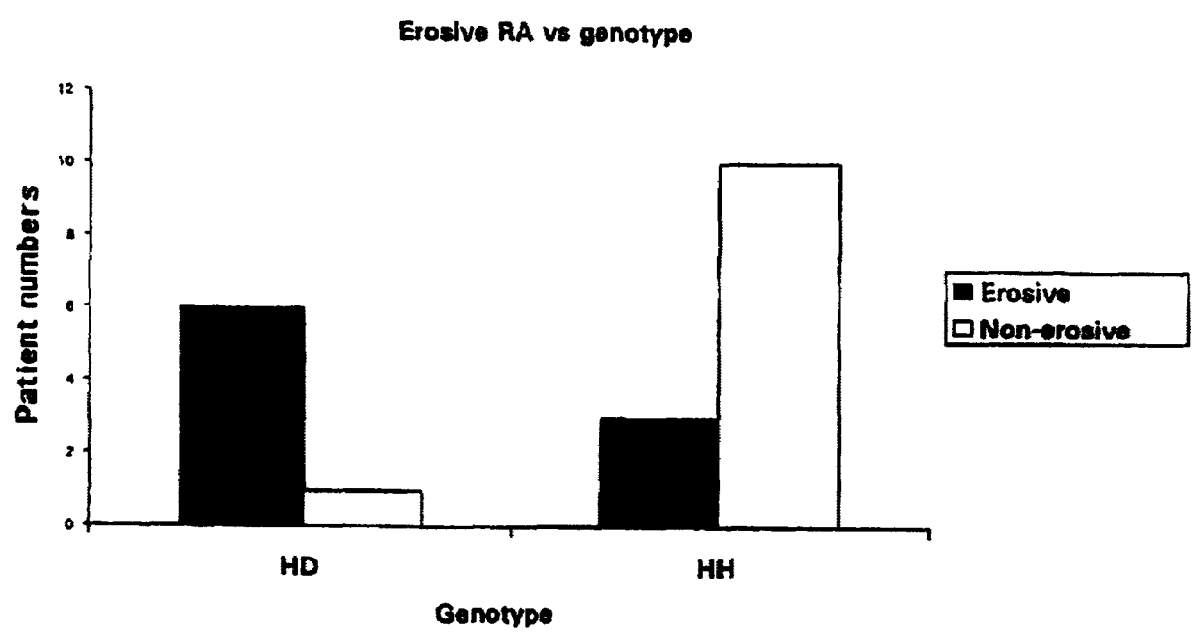

FIG. 21 provides a graph showing the proportion of erosive (black) versus non-erosive (white) RA among the two most common genotypes, homozygous (H6/H6) and heterozygous (H6/D6).

Figure 22:
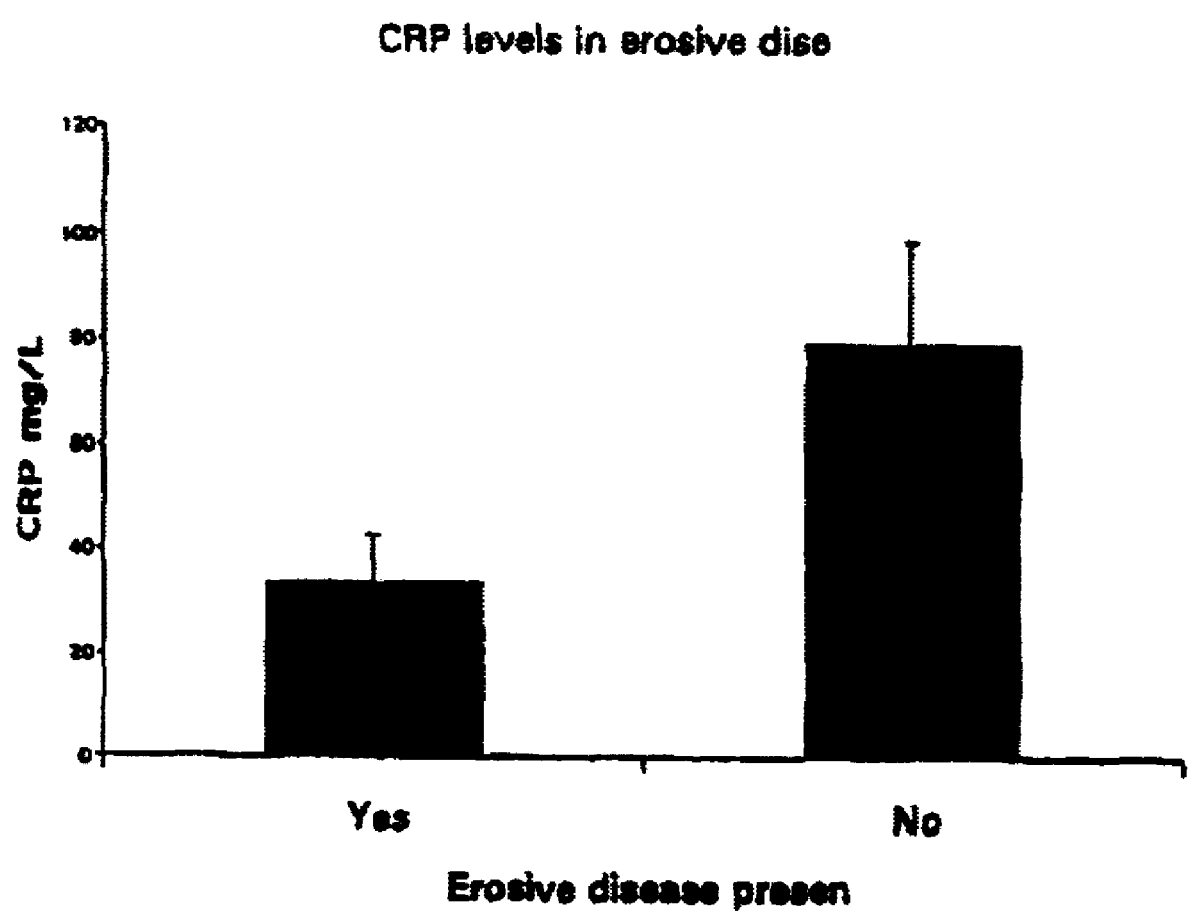

FIG. 22 shows a graph of CRP compared to the presence or absence of erosive RA.

Figure 23:
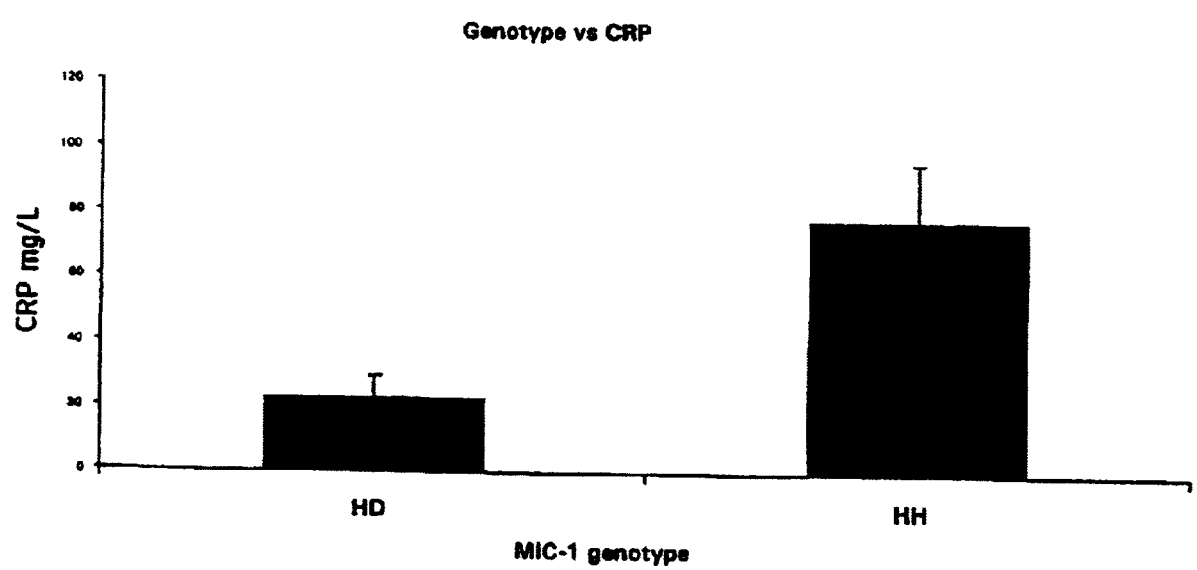

FIG. 23 provides a graph showing CRP compared to the homozygous (H6/H6) and heterozygous (H6/D6) genotypes.

EXAMPLE 1

Assessment of MIC-1 Expression in Pregnant Women

Methods:

Serum and Amniotic Fluid Samples:

Serum samples were obtained from 22 healthy pregnant women with a normal singleton pregnancy. No medication was being taken by any individual studied. In each case, gestational age was determined by an early pregnancy ultrasound scan. All women subsequently had a normal vaginal delivery at term (37-41 weeks) of a healthy normally grown infant. Serum samples were collected from 6 women between 10-14 weeks of pregnancy, and 8 women between 26-30 weeks and 37-40 weeks of pregnancy. The time periods indicated correspond to the end of each trimester. Samples corresponding to each trimester were pooled prior to measurement of MIC-1 levels. Serial maternal serum samples were also taken, on a weekly basis approximately, from 4 women from 30 weeks of gestation to delivery. Again, all four women were healthy with a normal singleton pregnancy and had a normal vaginal delivery at term of a normal healthy infant In addition, amniotic fluid was obtained from 10 women undergoing amniocentesis at 15-17 weeks of gestation for foetal ksryotyping. In all cases, the indication for karyotyping was advanced maternal age (>37 years). Amniotic fluid were also pooled prior to measurement of MIC-1 levels.

Placental Extracts:

Between 100-150 mg of placental tissue (rinsed 4-5 times in saline solution and frozen in liquid nitrogen and stored at −80° C.) was homogenised in 1 m. of phosphate-buffered saline (PBS). Homogenates were centrifuged at 10,000 rpm for 30 seconds and the supernatant transferred to tubes. Total protein was measured by the BCA total protein assay (Pierce) following the manufacturer's instructions. BSA solutions ranging between 0-1000 µg/ml were used as standard solutions.

BeWo Cell Culture:

The human choriocarcinoma trophoblastic cell line (BeWo) was purchased from ATCC (Rockville, Md.). Cells were seeded into 96 well tissue culture plates at 5000 cells per well in 250 µl of Dulbecco's Modification of Eagle's Medium DMEM (Gibco BRL) containig 4.5 g/l D-glucose, 110 mg/l sodium pyruvate, 0.584 g/l L-glutamine, 4 mg/l pyridoxine hydrochloride and 1x Nutridoma-SR (Boehringer Manmheim, Germany) and cultured at 37° C. in the presence of 5% carbon dioxide for 1-5 days. At this time, the culture plates were spun at 1000 rpm for 10 minutes and the supernatant was removed and stored at −20° C. until quantitation of MIC-1.

Reverse Transcriptase-polymerase Chain Reaction (RT-PCR) Analysis of MIC-1 mRNA Synthesis:

Total RNA was isolated from BeWo cell monolayers in 96-well plates using Tri-Pure Reagent (Roche) and the method provided by the manufacturer. Reverse transcription (RT) was carried out in a total reaction volume of 20 µl using 1 µg of RNA, a $poly(T)_{15}$ primer and 50 units of Expand Reverse Transcriptase (Roche) using the manufacturer's recommended conditions. A 5 µl aliquot of the RT reaction was amplified in a PCR reaction using Pfu polymerase (Promega) and primers;

(SEQ ID NO:5)
MSB-1 (5'-AGGACCTGCTAACCAGGCTGCGGGCCAACCAGAGC-3')
and (SEQ ID NO:8)
MSB-5 (5'-GGCTAACAAGTCATCATAGGTCTGGAGCGACAC-3'), which flank the single intron of MIC-1. PCR conditions were as follows: an initial denaturation step at 95° C. for 1 minute, followed by 35 cycles at 95° C. for 30 seconds, 60° C. for 30 seconds, 72° C. for 2 minutes. An RT reaction in which the RNA was omitted was used as a negative control, while a plasmid carrying the MIC-1 pre-pro-MIC/FLAG coding sequence (Bootcov et al., 1997) was included as a positive control. PCR products were separated on 0.8% (w/v) agarose gels.

Generation of MIC-1 Antibodies:

A sheep anti-MIC-1 polyclonal antibody (PAb) 233B3 was generated by immunisation with recombinant human MIC-1 (rhMIC-1), which was synthesised in accordance with the method described in International patent publication No. WO 97/00958, in Complete Freunds Adjuvant Additional boosts were given over a period of 6 months and the sheep were bled 10 days after the final injection. An enriched IgG fraction of normal sheep serum and 233B3 were prepared by caprylic acid precipitation followed by ammonium sulphate precipitation. The IgG enriched 233B3 fraction was designated 233-P.

A mouse anti-MIC-1 monoclonal antibody (MAb) secreting hybridoma was generated from mice immunised with rhMIC-1. Hybridomas were cultured in DMEM (Gibco BRL) containing 4.5 g/l D-glucose, 110 mg/sodium pyruvate, 0.584 g/l L-glutamine, 4 mg/l pyridoxine hydrochloride supplemented with 20% FCS (CSL, Melbourne). For MAb collection, the hybridomas were transferred into fresh DMEM-hi glucose supplemented with Nutridoma-SR (Boehringer Mannheim) for 7 days. The -culture supernatant's were spun at 2000 rpm for 10 minutes to remove cell debris and frozen until used. The sensitivity of the PAb and MAb preparations were examined by direct ELISA.

Direct ELISA:

Ninety-six well Maxsorp ELISA plates (Nunc) were coated (100 µl/well) with either 18 ng/ml rhMIC-1 or 20 ng/ml rhTGF-β1 (R&D Systems) in coating buffer (0.1M carbonate in distilled $H_2O$, pH 9.4-9.8) at 40° C. for 24 hours. Plates were then washed three times with 300 µl of wash buffer (PBS containing 0.05% (v/v) Tween-20 (Sigma)) and non-specific binding was blocked with 250 µl of 1% (w/v) BSA (Boehringer Aaheim) in PBS for 2 hours at 37° C. Hybridoma serum-free media containing the anti-MIC-1 MAb, sheep PAb 233B3-P diluted 1:500,000 in antibody diauant (PBS containing 1% (w/v) BSA and 0.05% (v/v) Tween-20), culture media conditioned by the mouse myeloma cell line SP2/0, DMEM+Nutridoma, immunoglobin G. enriched normal sheep serum diluted 1;500,000 in antibody diluant, 200 ng/ml mouse IgG1 (R&D Systems) in DMEM+Nutridoma, or antibody diluant alone were then added to the plates (100 µl/well) and incubated for 1 hour at 37° C. The plates were washed three times followed by the addition of 100 µl/well of biotinylated donkey anti-sheep IgG (Jackson Immunoresearch) or biotinylated goat anti-mouse IgG (Jackson Immunoresearch) diluted 1:10,000 in antibody diluant and incubated for 1 hour at 37° C. The plates were washed three times and 100 µl/well of horseradish peroxidase-conjugated streptavidin (Genzyme) diluted 1:2000 in antibody diluant was added to the plates and incubated for 30 minutes at 37° C. Plates were washed four times followed by the addition of 100 µl/well of peroxidase substrate (1 mg/ml o-phenylenediamine dihydrochloride (Sigma) in 0.05M phosphate-citrate buffer containing 0.014% $H_2O_2$, pH5.0 (Sigma)). Colour development was allowed to proceed for 5-15 minutes and was terminated by the addition of 100 µl/well of 4N $H_2SO_4$. The absorbance was measured at 490 nm in a microplate reader (Pasteur Diagnostics).

MIC-1 Sandwich ELISA:

A MIC-1 sandwich ELISA was established utilising the anti-MIC-1 mouse MAb for antigen capture and the sheep PAb 233-P for detection. The optimum concentration of both antibodies was determined empirically then used for all subsequent studies. Ninety-six well Maxisorp ELISA plates were coated with anti MIC-1 MAb supernatant diluted 1:5 (final immunoglobin concentration was approximately 20 ng/ml) in coating buffer at 40° C. for 24 hours. Plates were then washed three times with 300 µl of wash buffer and non-specific binding was blocked with 250 µl of 1% (w/v) BSA in PBS for 2 hours at 37° C. rhMIC-1 standards, tissue culture supernatant, maternal serum, placental extracts, or amniotic fluid diluted in antibody diluant, were then added to the plates (100 µl/well) and incubated for 1 hour at 37° C. The plates were washed three times followed by the addition of 100 µl/well of the sheep PAb 233-P diluted 1:5000 in antibody diluant and incubated for 1 hour at 37° C. The plates were then washed three times and 100 µl/well of biotinylated donkey anti-sheep IgG diluted to 1:5000 in antibody diluant was added and incubated for 1 hour at 37° C. The plates were then developed as for the direct ELISA. The concentration of hMIC-1 in the samples was determined by comparison with the rhMIC-1-standard curve. The level of rhMIC-1 in this standard curve was determined on the basis of total protein content and thus in terms of absolute amount is subject to significant error. However, as the same standards were used throughout, this makes no difference to the relative values estimated in this example. All samples were assayed in triplicate on at least two occasions. Results are presented as the mean +/− SD. The sensitivity of the MIC-1 sandwich assay was assessed by testing with up to 500 pg/ml amounts of TGF-β1 and inhibin-A (which are both members of the TGF-β superfamily).

Immunoprecipitation:

Immunoprecipitation was carried out using 0.2 ml hybridoma serum-free media containing the anti-MIC-1 MAb adsorbed to protein-A Sepharose. Serum and medium samples (1 ml) were incubated with these antibodies overnight at 40° C. then washed 5 times with PBS containing 1% (v/v) Triton X-100. Bound proteins were eluted using non-reducing sodium dodecyl sulphate (SDS)-sample buffer and analysed by SDS-polyacrylamide gel electrophoresis (SDS-PAGE) (Laemmi, 1970) followed by immunoblot analysis with the sheep polyclonal antibody 233-P. Immunoblot analysis was performed essentially as described by Bootcov et al., (1997) except that polyclonal antibody 233-P was used as primary antibody at a dilution of 1:7000 and the secondary antibody was donkey anti-sheep Ig-biotin at a dilution of 1:5000.

Figure 1:
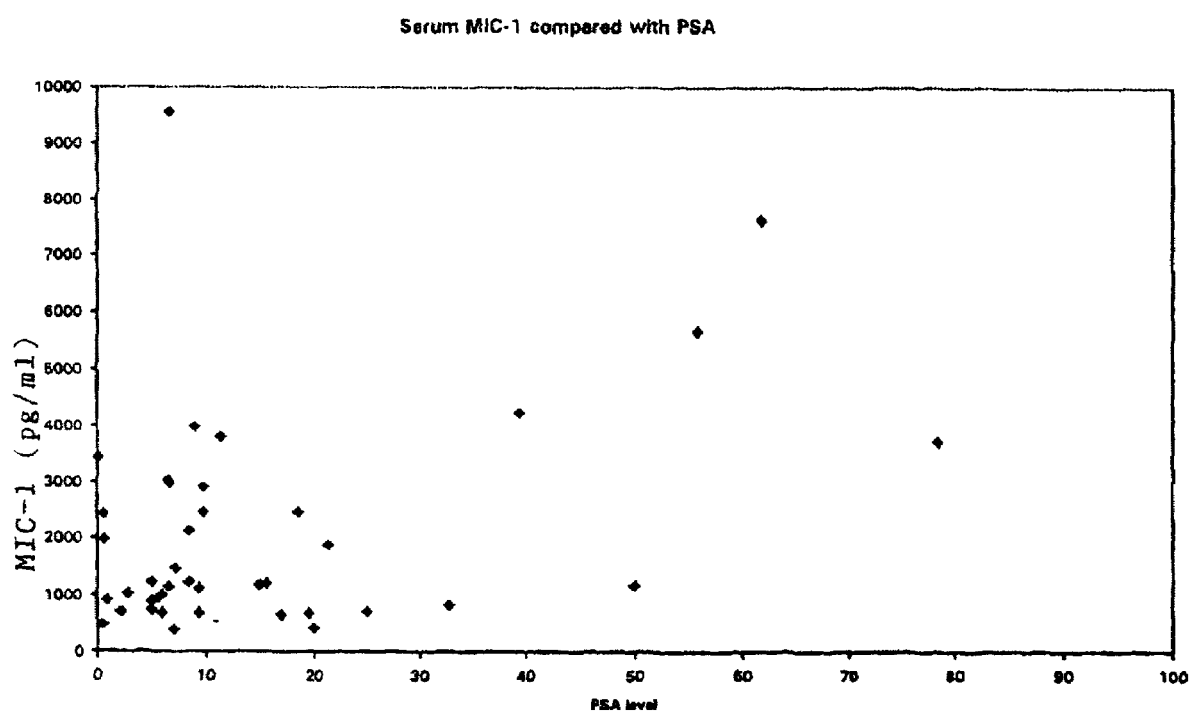
Figure 2:
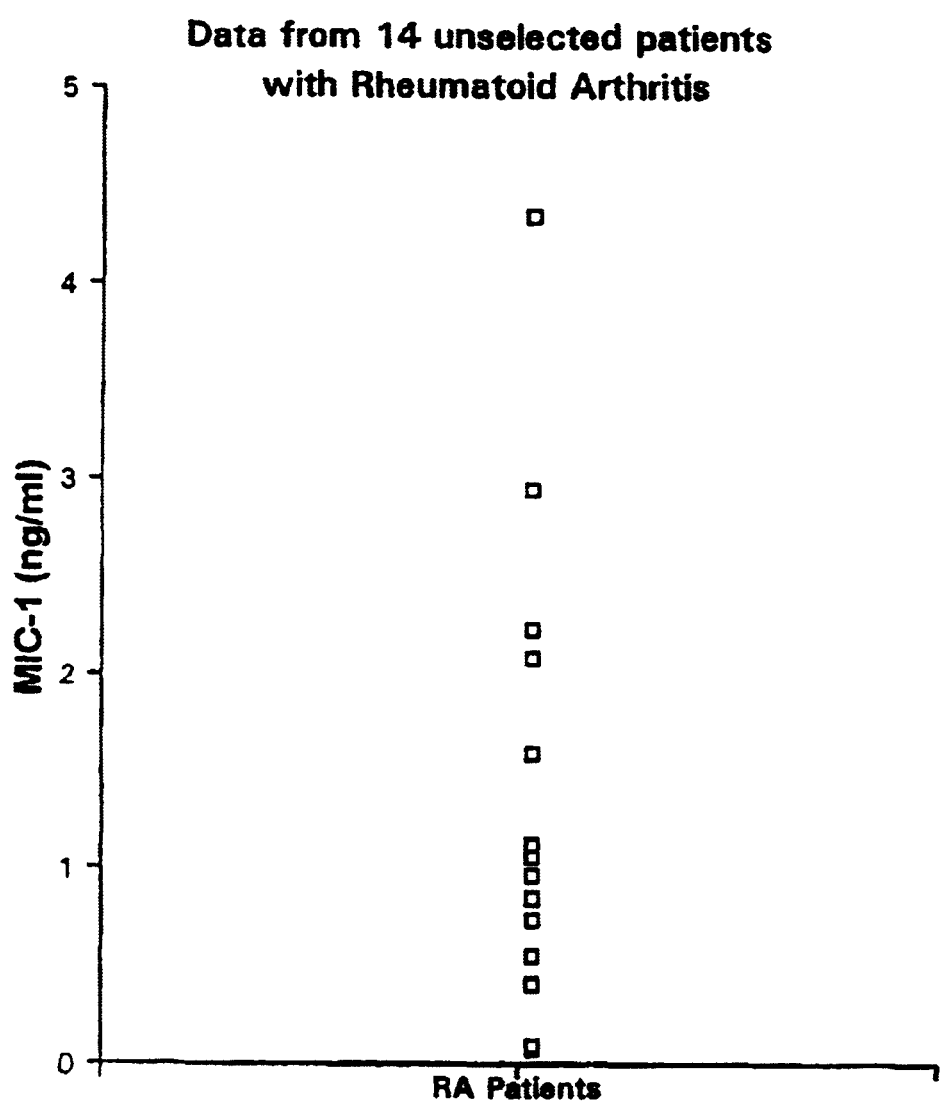
Figure 4:
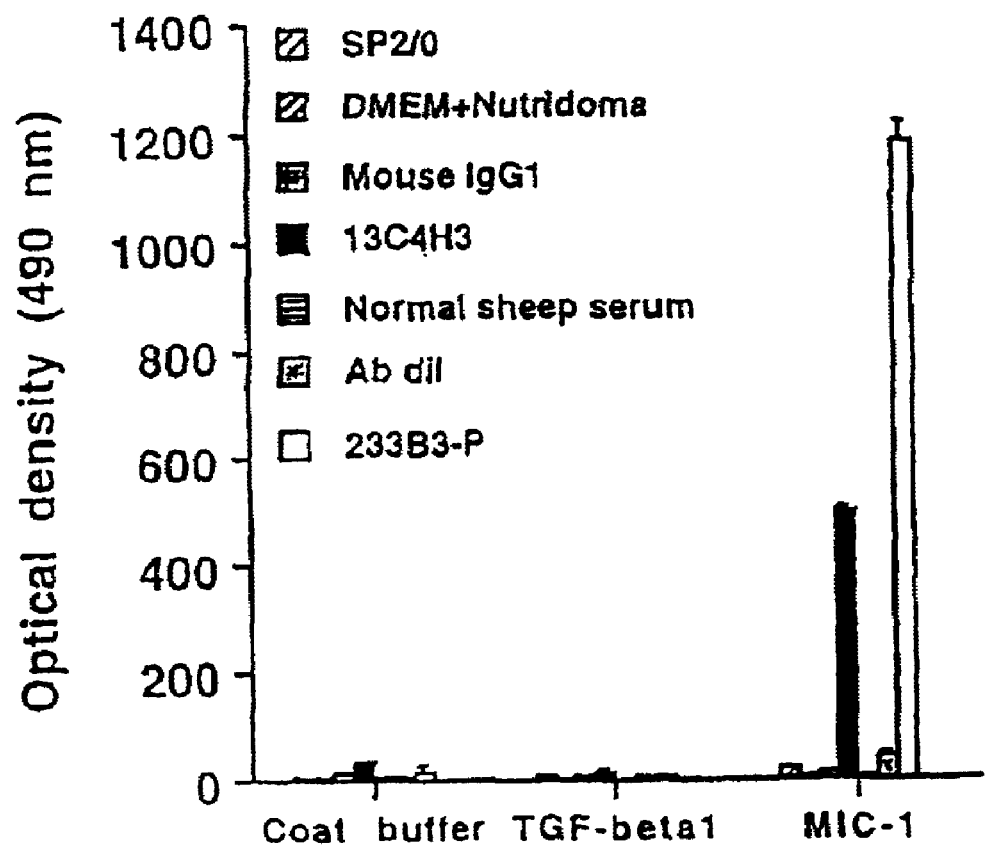

Results:

Sensitivity of Anti-MIC-1 PAb and MAb:

The ability of the sheep PAb 233-P and the mouse MAb to bind to rhMIC-1 was examined by direct ELISA. It was found that both undiluted tissue culture supernatant containing the MAb and the sheep PAb 233-P at a dilution of 1:500,000 in antibody diluant bound strongly to 1.8 ng immobilised rhMIC-1 (FIG. 4). Neither culture media conditioned by the mouse myeloma cell line SP2/0, unconditioned culture media, mouse IgG1, immunoglobin enriched normal sheep serum, or antibody diluant reacted with rhMIC-1. Minimal background binding to uncoated wells was observed for all samples examined. No reactivity was detected when either the anti-MIC-1 MAb or polyclonal antibody 233-P were incubated with immobilised: rhTGF-$\beta$1.

Figure 5:
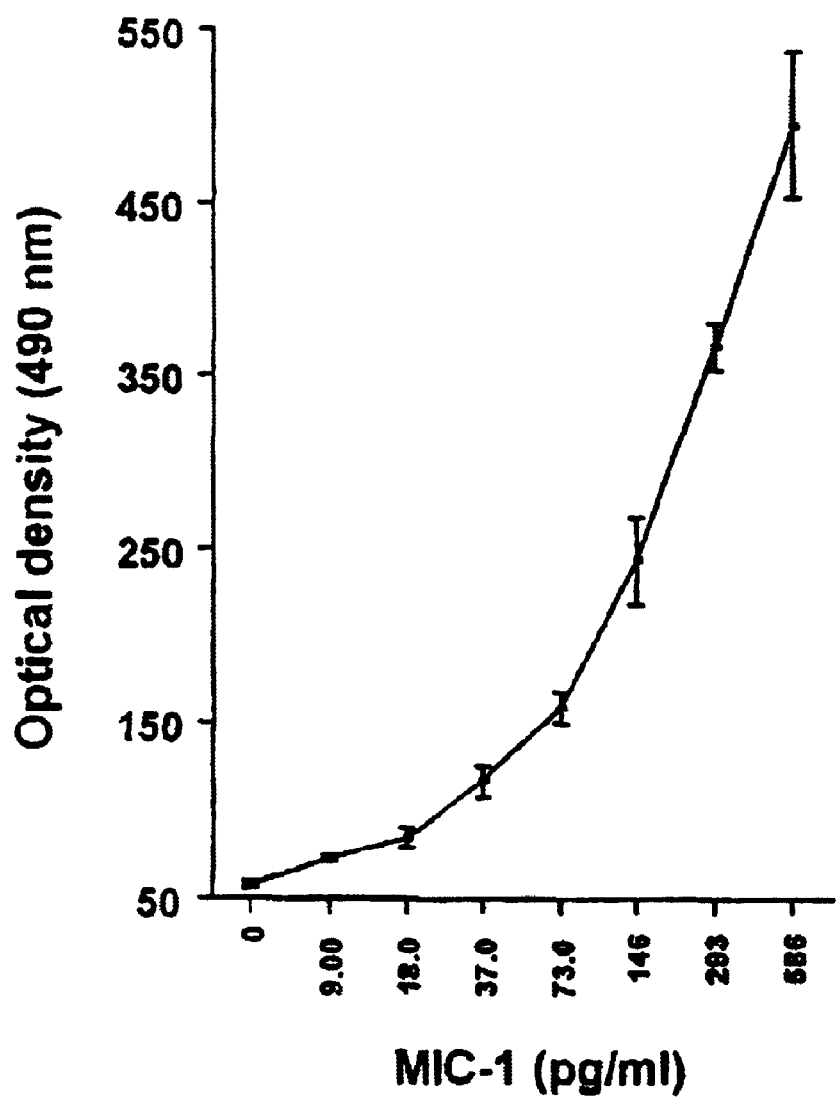

MIC-1 Sandwich ELISA:

A sandwich ELISA employing the anti-MIC-1 MAb and the PAb 233-P was established which could accurately quantify rhMIC-1 in the Age of 10-500 pg/ml (FIG. 5). To examine the effect of factors present in human serum and culture media on estimation of this cytokine, 500 pg/ml of rhMIC-1 was added to antibody diluant containing either 10% (v/v) normal human serum or 10% (v/v) DMEM+Nutridoma and then quantified. It was found that the sandwich ELISA was accurate to within 5% of the correct value. Run to run variation was less than 5%. In sandwich ELISA with TGF-$\beta$1 and inhibin-A, no cross-reaction with these structurally related cytokines was observed.

Figure 6A:
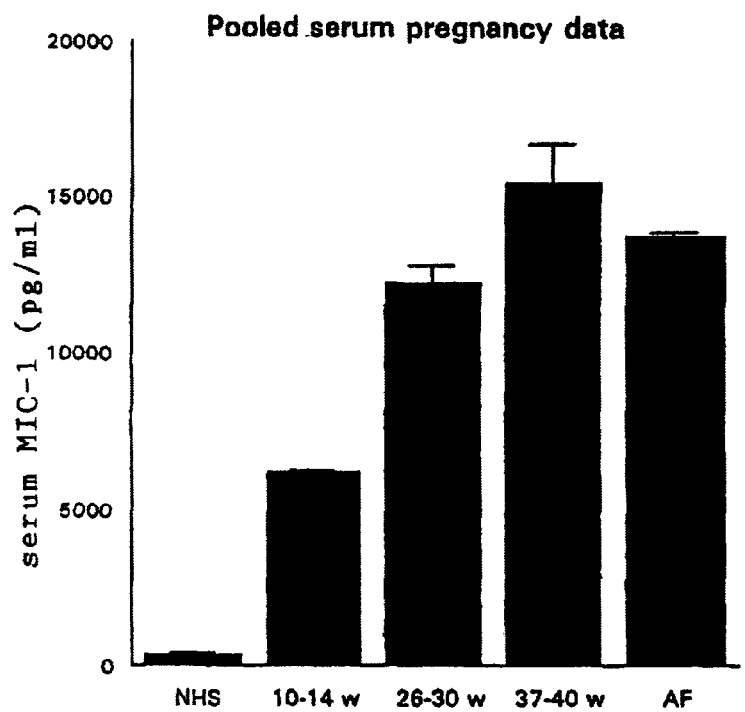

MIC-1 Levels in Staged Maternal Pregnancy Sera Increase During Pregnancy:

Pooled serum samples were diluted between 1:5-1:20 in antibody diluant prior to MIC-1 quantitation by sandwich ELISA. It was determined that pooled normal human sera contained approximately 0.36 (+/-0.04) ng/ml MIC-1 (FIG. 6A). In pooled maternal serum, the MIC-1 concentration was found to increase dramatically during pregnancy. Maternal serum samples corresponding to the first trimester contained approximately 6.3 (+/-0.02) ng/ml MIC-1, which rose to 12.24 (+/-0.54) ng/ml during the second trimester, and peaked at 15.3 (+/-1.31) ng/ml during the third trimester.

Figure 6B:
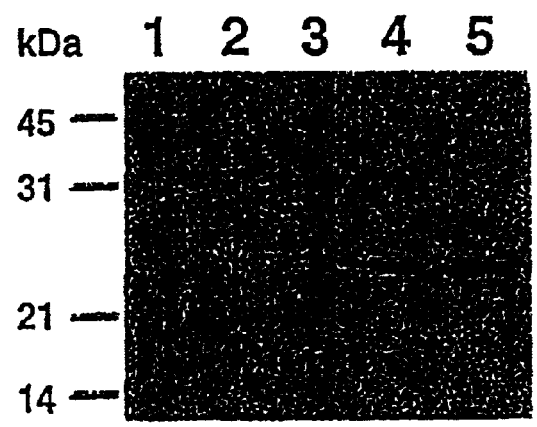

Immunoprecipitation was used to confirm the presence of MIC-1 in pooled maternal serum samples during pregnancy. MIC-1 was visualised by immunoprecipitation with the ant-MIC-1 MAb followed by immunoblot analysis with PAb 233B3-P. A band corresponding to the disulphide linked mature MIC-1 peptide (approximately 25 kDa) can be observed in the second and third trimester pregnancy serum samples FIG. 6B, lanes 3-4). The highest level of MIC-1 was found in the third trimester sample. No similar band was observed in normal serum or the sample corresponding to the first trimester due to the lower sensitivity of immunoblot analysis (FIG. 6B, lanes 1-2).

Figure 7:
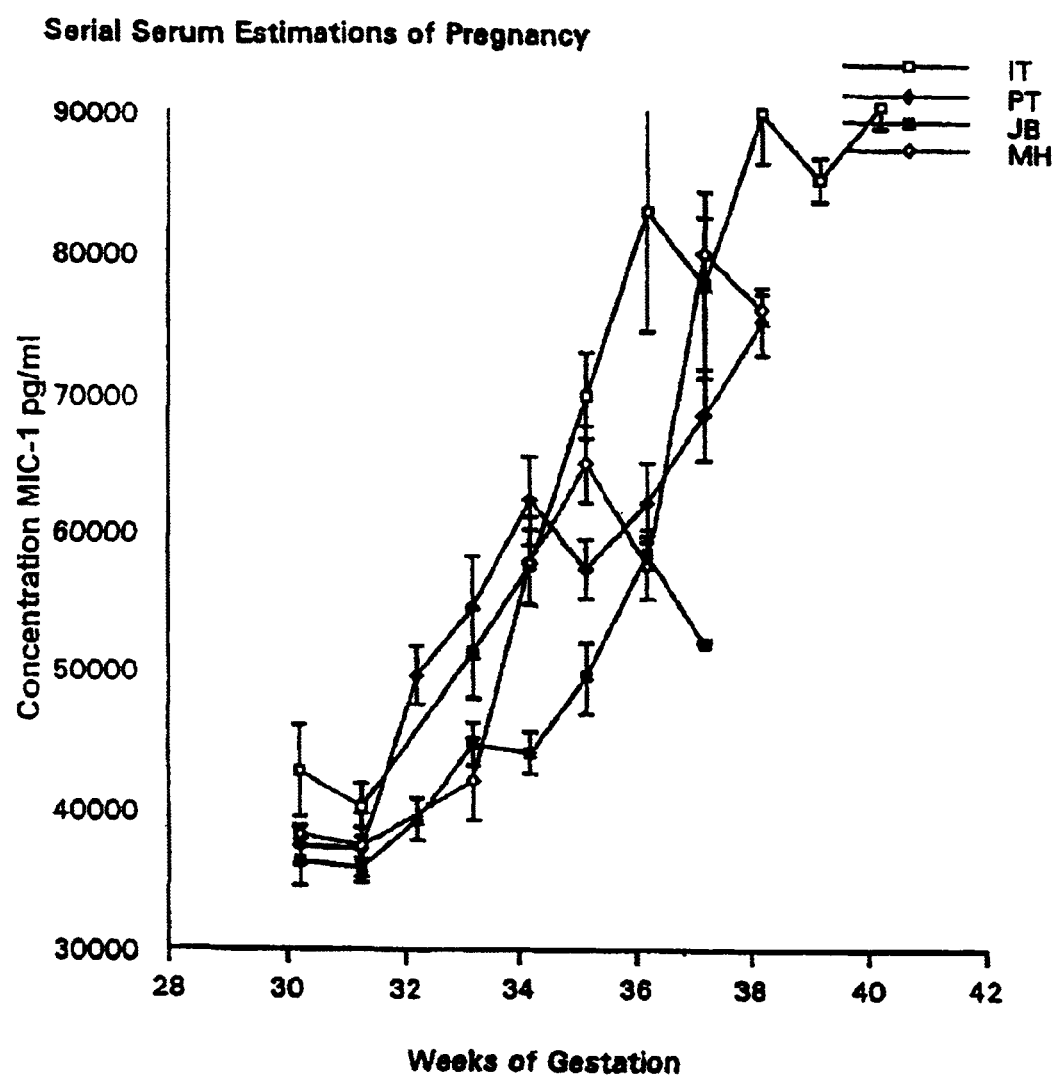

Maternal-serum MIC-1 concentrations were also examined in serial samples from four pregnant women. At 30 weeks of gestation, serum from all four women examined contained approximately 4 ng/ml MIC-1 (FIG. 7). Maternal serum MIC-1 levels were found to increase from 30 weeks of gestation until birth. Subjects designated MH and JB exhibited a slight decrease in MIC-1 maternal serum levels over the last week of pregnancy.

MIC-1 can be Detected in Amniotic Fluid:

In addition to maternal serum, amniotic fluid collected from 10 women during the second trimester for karyotyping purposes was pooled prior to quantification of MIC-1 levels by sandwich ELISA. It was determined that the pooled amniotic fluid sample contained approximately 13.68 (+/-0.16) ng/ml MIC-1 (FIG. 6A). Immunoprecipitation and western blot analysis of pooled amniotic fluid revealed a band of approximately 25 kDa, which corresponds to the disulphide linked mature MIC-1 peptide (FIG. 6B, lane 5).

Figure 8:
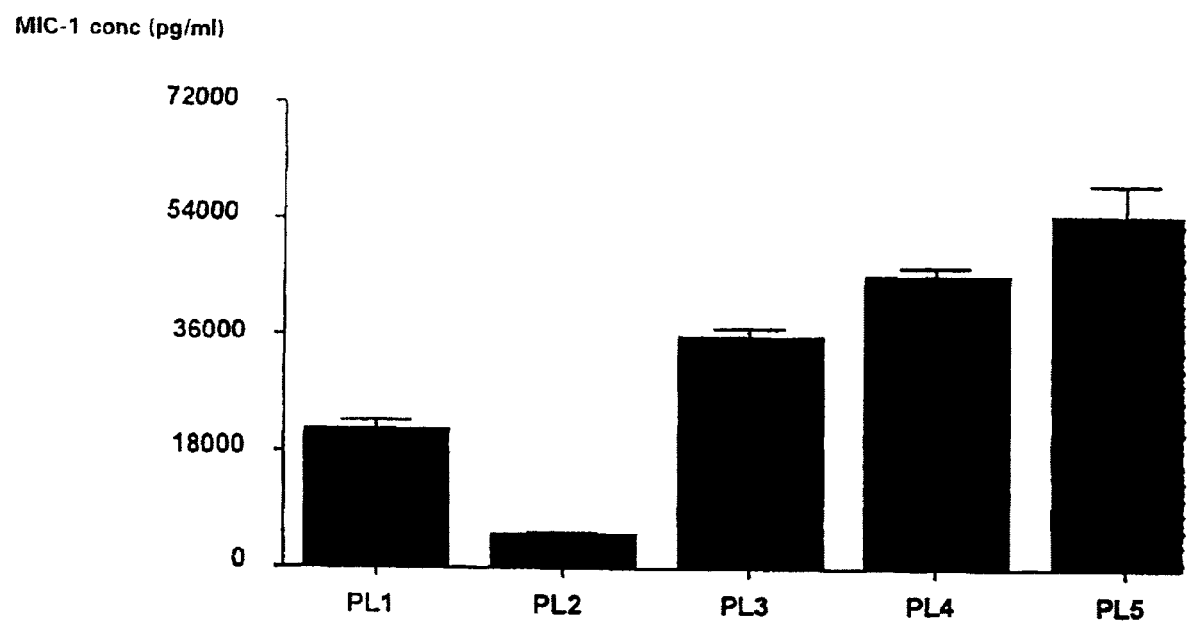

MIC-1 can be Detected in Human Placental Extracts:

In order to test whether the placenta is a major source of circulating MIC-1 in the serum of pregnant women, 5 human placenta extracts were examined for the presence of MIC-1 by sandwich ELISA. All five samples were found to be positive for MIC-1 (FIG. 8), ranging in concentration from 5.04-54 ng/ml. Significantly the sample designated PL2, which was the only one derived from a premature birth, contained much lower levels of MIC-1 than the other samples.

Figure 9A:
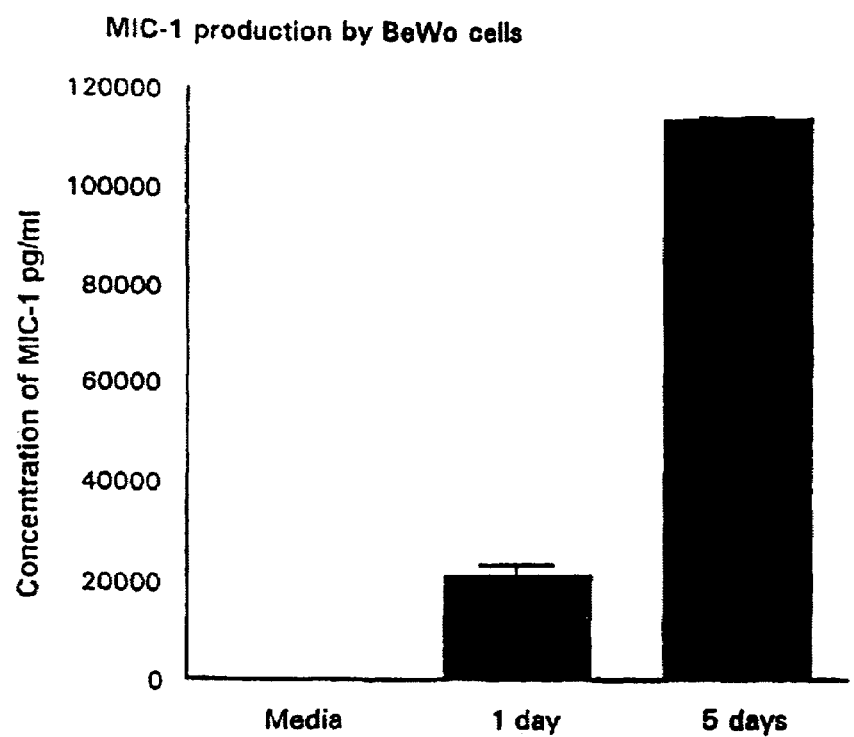
Figure 9:
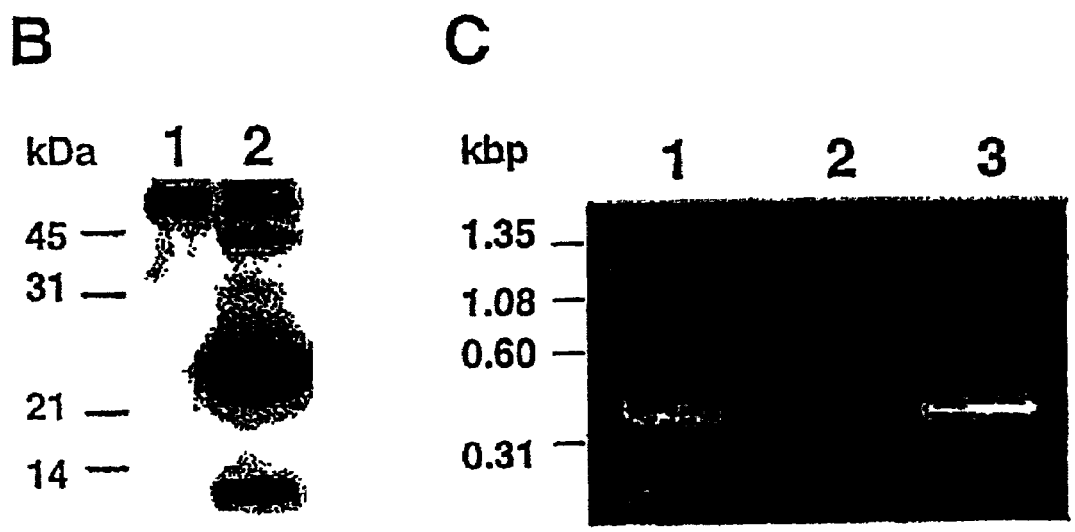

Cultured BeWo Cells Constitutively Express MIC-1 RNA and Secrete Mature MIC-1:

As high levels of MIC-1 were detected in placental extracts it seemed likely that the placental trophoblastic cell line, BeWo, also produces this cytokine. An examination of tissue culture media conditioned by BeWo cells under resting conditions for the presence of secreted MIC-1 by sandwich ELISA was therefore conducted. It was determined that media used to culture BeWo cells for 24 hours contained approximately 21.6 (+/-2.95) ng/ml MIC-1 (FIG. 9A). The concentration of MIC-1 in the culture media after a five day incubation increased to approximately 117 (+/-7.2) ng/ml. The ability of unstimulated BeWo cells to secrete MIC-1 was also examined by immunoprecipitation and western blot analysis. High levels of secreted mature MIC-1, as indicated by a band at approximately 25 kDa, were observed in media condition by BeWo cells for 5 days (FIG. 9B). Additional bands migrating at 55 Da and 12.5 kDa bands were observed, which may represent incompletely processed MIC-1 hemi-dimer and monomer respectively. Culture media which had not been exposed to BeWo cells contained no detectable MIC-1 when examined by sandwich ELISA or by immunoprecipitation.

RT-PCR was used to investigate the presence of the MIC-1 transcript in unstimulated BeWo cells. Total RNA was extracted from BeWo cells cultured for 24 hours and subjected to RT-PCR as described. A single product of 0.4 kbp was observed, indicating that the MIC-1 transcript was present in BeWo cells (FIG. 9C). No product was detected in the absence of BeWo or plasmid DNA.

Discussion:

The results of Example 1 indicate that MIC-1 is present in large amounts in maternal sera and that levels rise substantially with advancing gestation.

Whilst elevated levels of MIC-1 occur in maternal serum during pregnancy, this does not necessarily mean that the developing foetus is exposed to this cytokine. However, the detection of MIC-1 in amniotic fluid represents direct evidence for foetal exposure. The level of MIC-1 in amniotic fluid was comparable to that present in second and third trimester maternal serum and well in excess of that present in normal human serum. During pregnancy the foetus ingests large amounts of amniotic fluid and may also absorb amniotic fluid via the thin foetal epidermis. These findings therefore provide strong evidence that the developing foetus is exposed to high concentrations of MIC-1.

In order to investigate whether maternal serum and amniotic fluid MIC-1 originates from a foetal or maternal source, MIC-1 in human placental extracts was measured and this demonstrated that they contain large amounts of MIC-1 protein. Interestingly, the quantity of MIC-1 present in 4 of the 5 placental extracts (>18 ng/ml) was higher than that detected in pooled maternal sera and amniotic fluid. Using immunohistochemistry and in situ hybridisation it has been demonstrated that the MIC-1 transcript and protein is present in the terminal villi of the placenta (Parallar et al., 1998), a structure rich in syncitiotrophoblasts. It is therefore reasoned that the BeWo human trophoblastic cell line may synthesise and secrete this cytokine. The BeWo cells constitutively express the MIC-1 transcript and secrete large amounts of MIC-1 under resting conditions. These findings suggest that the trophoblastic cells within the placenta are a major source of the MIC-1 present in maternal serum and amniotic fluid. However, the localisation of the MIC-1 transcript and protein to the developing epidermis in day 18 rat embryos (Paralkar et al., 1998) suggests the embryo may also contribute to the MIC-1 levels observed.

The precise role of MIC-1 during pregnancy is unknown. However, based upon the results described above and experimentation reported elsewhere, it appears that MIC-1 has an immunomodulatory role during pregnancy. For example, it has been reported previously that rhMIC-1 inhibits the release of pro-inflammatory cytokines from LPS-activated macrophages (Bootcov et al., 1997). Further, MIC-1 is known to suppress the formation of erythrocyte and granulocyte/macrophage cell lineages from normal human non-adherent T-cell depleted marrow cells (Hromas et al., 1997). These findings indicate that MIC-1 is a broad inhibitor of inflammation, suppressing both the development of the monocyte/macrophage lineage and their ability to produce pro-inflammatory mediators.

Intrauterine inflammation accompanying pro-inflammatory cytokine production has been associated with foetal rejection or preterm labour (Romero et al., 1992; Hillier et al., 1993; Opsjon et al., 1993). In this context, the present applicants consider that MIC-1 present in the placenta and amniotic fluid acts to maintain pregnancy by suppressing the production of pro-inflammatory cytokines within the uterus. The finding in the present example that placental extracts derived from a premature labour contained depressed concentrations of MIC-1 when-compared to normal pregnancies provides strong support for this.

EXAMPLE 2

MIC-1 Variant Detection Detection and Genotyping by Immunoassay

In the process of cloning MIC-1 it was realised that there were at least two alleles of this TGF-β superfamily cytokine. In subsequent investigation of human material it was confirmed that the 2 alleles were represented in the general community. These alleles differ by a point mutation yielding a change from histidine at position 6 of the amino acid sequence of mature normal or "wild type" MIC-1 (H6), to an aspartic acid at position 6 (D6). This represents a non-conservative substitution of a weakly basic, aromatic amino acid to a strongly acidic, acyclic amino acid.

Methods and Results:

Generation of Anti-MIC-1 Antibodies:

Anti-MIC-1 monoclonal antibody (MWb) secreting hybridomas were generated from mice immunised with recombinant human MIC-1 (rhMIC-1), which was produced in yeast (*Pichia pastoris*) in accordance with the method described in International patent publication No. WO 97/00958. Hybridomas were cultured in DMEM (Gibco BRL) containing 4.5 g/l D-glucose, 110 mg/l sodium pyruvate, 0.584 g/l L-glutamine, 4 mg/l pyridoxine hydrochloride supplemented with 20% FCS (CSL, Melbourne). For MAb collection, the hybridomas were transferred into fresh DMEM-hi glucose supplemented with Nutridoma-SR (Boelringer Mannheim) for 7 days. The culture supernatant's were spun at 2000 rpm for 10 minutes to remove cell debris and frozen until used.

The collected Mabs were subjected to epitope mapping studies using Western blot analysis an extensive panel of MIC-1 relatives, mutants and chimaeras. None of the Mabs was able to cross-react with either the murine homologue of MIC-1 or with hTGF-β1, and all of the Mab epitopes were conformation-dependent. A distinct cross-reactivity pattern with the various antigens was observed for each of the Mabs suggesting the presence of at least five immunogenic regions on the MIC-1 surface. Two of the Mabs (13C4H3 and 26G6H6) were selected for further study on the basis of their high affinities (each having ED50's in the range of 1.3-2.5× $10^{-9}$ M).

Mab 13C4H3 was found to bind to the amino terminus (positions 1-13) of mature human wild type MIC-1 (i.e. with histidine at position 6) with significantly greater affinity than that of the corresponding epitope of $Asp^{202}$-MIC-1, and is therefore able to discriminate between human wild type MIC-1 and $Asp^{202}$-MIC-1. As Mab 13C4H3 was unable to recognise a murine-human MIC-1 chimaera (wherein all of the amino acids of the amino terminus (1-13) which are dissimilar to the human sequence, were replaced with the corresponding amino acids of human MIC-1), it was concluded that additional residues outside of the amino terminus which differ between the human and mouse proteins are possibly also involved.

Mab 26G6H6 was found to be directed against an epitope (comprising amino acids in the region of positions 24-37, 56-68 and 91-98 of mature human wild type MIC-1) located near the tips of the so-called "fingers" of MIC-1. Mab 26G6H6 did not discriminate between MIC-1 proteins having histidine or aspartic acid at position 6.

These antibodies therefore enable the detection of heterozygote and homozygote individuals by measuring bound MIC-1 levels in immunoassays. That is, with Mab 13C4H3 it would be expected that maximal binding would be observed with H6/H6 homozygotes and zero binding with D6/D6 homozygotes, while an intermediate (e.g. 50%) level of binding would be expected with H6/D6 heterozygotes.

The epitope binding specificities of the above anti-MIC-1 antibodies are described in detail in Fairlie et al., 2001.

Total MIC-1 Determination Using 26G6H6:

ELISA plates (Maxisorb, Nunc) were coated for 24 hours at 4° C. with 80 μl, 1:500 of 26G6H6 in bicarbonate buffer pH 9.4-9.8 with care taken to prevent significant evaporation, samples were diluted 1:3-1:100, depending on estimated MIC-1 concentration, in Sample buffer (1% w/v BSA (Progen), 0.05% v/v Tween (Sigma) in PBS, pH 7.2, and a MIC-1 "Standard" prepared by diluting 1 μg/ml rhMIC-1 (in 1% BSA w/v, 3 mM HCl) 1:1000 in sample buffer followed by eight doubling dilutions (1000 pg/ml-7.8 pg/ml).

Assays were conducted as follows:

Coated plates were washed three times with wash buffer (0.05% v/v Tween in PBS) 300 μl/well. Blocking was performed by incubation with 250 μl 1% BSA w/v at 21 DegC for 1 hour. Blocking buffer was then removed and 100 μl/well of standards or samples added without intervening washing for 1 hour at 21° C. Subsequently, the detection antibody, 233-P, 1:25000, in sample buffer v/v, was added, 100 μl/well and incubated for 16 hours at 4° C. Donkey, anti-sheep, biotinylated IgG (Jackson's Laboratories) 1:5000 in sample buffer v/v, 100 µl/well, was then added and incubated for 1 hour at 21° C. followed by incubation with Streptaviden-HRP conjugate (Genzyme) 1:2000 in sample buffer v/v, 100 µl/well, for 30 minutes at 21° C. OPD (Sigma) 0.4 mg/ml, in the manufacturer's recommended buffer, was incubated at 100 µl/well until a clear difference was seen between the 7.8 pg/ml standard and the zero standard. The 1000 pg/ml standard should have an OD of at least greater than one. Finally, the reaction was stopped with 100 µl/well of 2N $H_2SO_4$.

Plates can be read at 490 nm and a standard curve constructed using a two binding site hyperbole. Sample values are extrapolated from this curve.

The plates were washed with 300 µl/well of wash buffer after each step from before the addition of the detection antibody 233-P till the addition of OPD.

Sensitivity and Specificity of anti-MIC-1 PAb and Mab:

The ability of the sheep PAb 233-P and the mouse MAb 13C4H3 to bind to rhMIC-1 was examined by direct ELISA. It was found that both undiluted tissue culture supernatant containing the MAb 13C4H3 and the sheep PAb 233-P at a dilution of 1:500 000 in antibody diluent bound strongly to 1.8 ng immobilised rhMIC-1. No reaction was observed between rhMIC-1 and culture media conditioned by the mouse myeloma cell line SP2/0, unconditioned culture media, mouse IgG1, immunoglobin enriched normal sheep serum, or antibody diluent. Minimal background binding to uncoated wells was observed for all samples examined. No reactivity was detected when either 13C4H3 or 233-P were incubated with immobilised rhTGF-β1.

Figure 10:
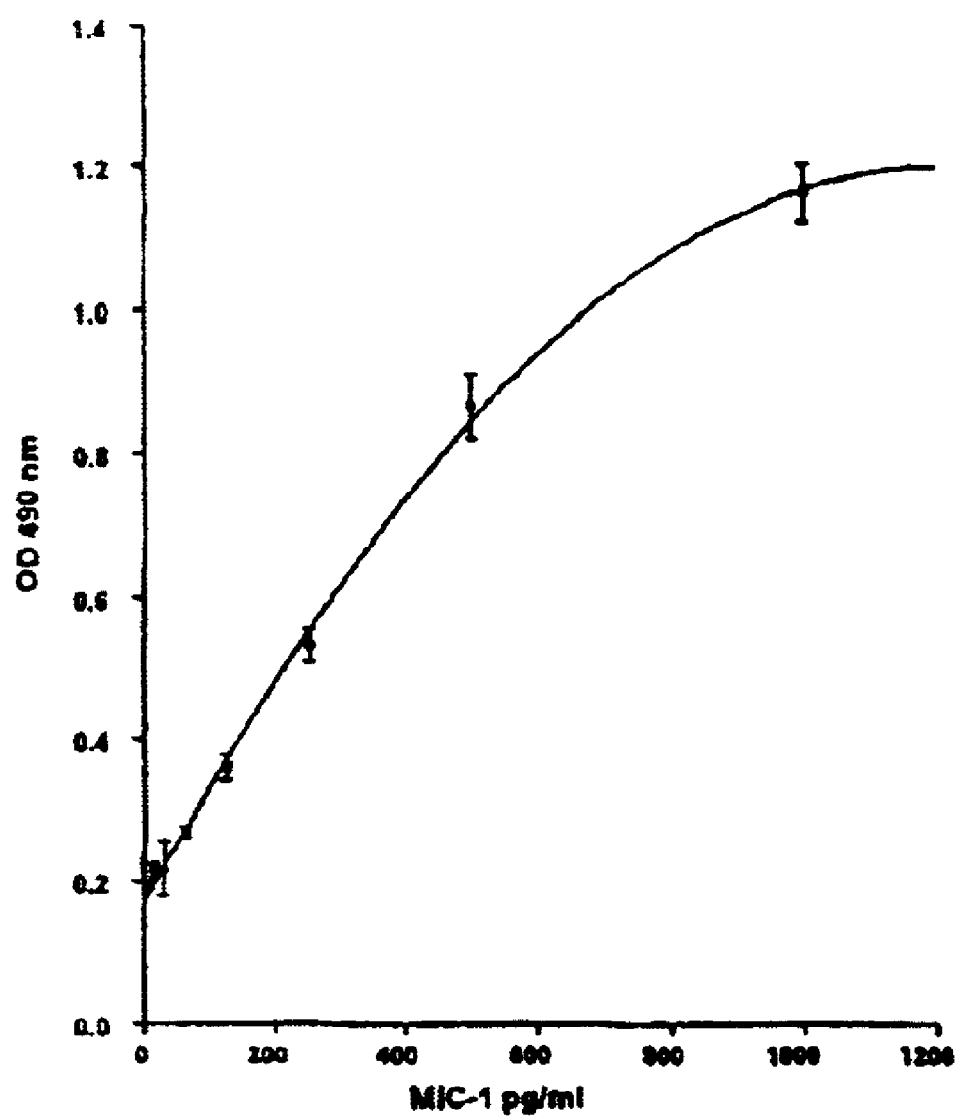

Specificity of the antibodies was determined by immunoprecipitation of purified rhMIC-1 with MAb 13C4H4 and 26G6H6, followed by immunoblot analysis with various MIC-1 specific antibodies. All the MIC-1 antibodies specifically recognised the 25 kD dimeric MIC-1. Additionally, blocking of the antibodies was performed by pre-incubating the antibody with purified rhMIC-1, prior to Western Blot analysis. This greatly reduced the interaction of the antibody with the MIC-1 specific 25 kD band, confirming specificity of the antibodies Mab 13C4H4, 26G6H6 and 233-P. Furthermore, those antibodies tested, failed to recognise inhibin, another member of the TGF-β superfamily. A typical assay standard curve is shown in FIG. 10 with error bars representing one standard deviation.

Determination of MIC-1 Genotype Using 13C4H4:

The higher affinity of the detection antibody 233-P, to a multitude of MIC-1 epitopes, compared to 13C4H4 led to a greater difference in the detected MIC-1 between the H6 and D6 alleles. This difference is a function of the differing affinities of the H6 and D6 epitopes to 13C4H4. The presence of 233-P, in a long incubation, leads to progressively less D6 being bound to the capture antibody, 13C4H4. These, now unbound, molecules become progressively bound to the higher affinity components of the polyclonal antibody that are specific for the 13C4H4 binding site. These molecules are now excluded from measurable MIC-1.

Another effect is also observed. That is, each molecule of MIC-1 that is excluded from binding the capture antibody excludes a multiple of 233-P antibodies. This occurs as 233-P is polyclonal and binds to multiple parts of the MIC-1 molecule. The result is that these immune complexes, between MIC-1 and 233-P, are excluded from the assay. As the 233-P antibody is the major contributor to background, the observed difference in MIC-1 concentration is further magnified. In the case of a homozygous D6/D6 genotype, the background staining is reduced to the point that a reading below the zero is obtained over wide concentration differences. In the case of the H6 allele, the rate of MIC-1 becoming free to bind the polyclonal antibody, solely, is much less, creating a wider difference in observed MIC-1 concentration.

The two sandwich enzyme linked immunosorbant assays involved in the determination of the MIC-1 concentration and MIC-1 allele in a particular sample, use 26G6H6 and 13C4H4 as the capture antibodies, respectively. The samples analysed may be from tissue culture (tissue culture medium or cell extract), human serum or plasma, or any human sample that is in fluid phase or may be processed into fluid phase by any process.

The assays used ELISA plates (Maxisorb, Nunc) coated for 24 hours at 4° C. with 80 µl, 1:500 of 13C4H4 in bicarbonate buffer pH 9.4-9.8 (care should be taken to prevent significant evaporation). Samples were diluted 1:3-1:100, depending on estimated MIC-1, determined in 13C4H4 assay concentration, in Sample buffer (1% w/v BSA (Progen), 0.05% v/v Tween (Sigma) in PBS, pH 7.2. The sample concentration should be between 50 and 150 pg/ml. The MIC-1 Standard (1 µg/ml recombinant MIC-1 in 196 BSA w/v, 3 mM HCL) was diluted 1:1000 in sample buffer and eight doubling dilutions then performed (1000 pg/ml-7.8 pg/ml).

The assays were conducted as follows:

Coated plates were washed three times with wash buffer (0.05% v/v Tween in PBS) 300 µl/well. Blocking was performed by incubation with 250 µl 1% BSA w/v at 21° C. for 1 hour. Blocking buffer was then removed and 100 µl/well of standards or samples added without intervening washing for 1 hour at 21° C. The detection antibody, 233-P, 1:10000, in sample buffer v/v, was added, 100 µl/well and incubated for 16 hours at 4° C. Donkey, anti-sheep, biotinolated IgG (Jackson's Laboratories) 1:5000 in sample buffer v/v, 100 µl/well, was then added and incubated for 1 hour at 21° C. followed by incubation with Streptaviden-HRP conjugate (Genzyme) 1:2000 in sample buffer v/v, 100 µl/well, for 30 minutes at 21° C. OPD (Sigma) 0.4 mg/ml, in the manufacturer's recommended buffer, was incubated at 100 µl/well until a clear difference was seen between the 7.8 pg/ml standard and the zero standard. The 1000 pg/ml standard should have an OD of at least greater than one. The reaction is stopped with 100 µl/well of 2N $H_2SO_4$.

Plates were read at 490 nm and a standard curve constructed using a two binding site hyperbole model. Sample values can be extrapolated from this curve.

The plates were washed with 300 µl/well of wash buffer after each step from before the addition of the detection antibody 233-P till the addition of OPD.

Discussion:

To determine the MIC-1 allele, the observed MIC-1 concentration, obtained from the 13C4H6 assay was divided by the total MIC-1 concentration, determined in the 26G6H6 assay. The cut-off ratios for the various alleles were determined by homozygous H6/H6 and D as well as heterozygous (HD) controls used in both assays. Validation data was included as set out below.

A ratio of less than 0 indicates a homozygous D6/D6 genotype, 0-0.6 is heterozygous and greater than 0.7 is homozygous H6/H6. It is noted that there are ratios greater than 1. Because of the dynamics of the assay, with regard to homozygous D6/D6 protein, higher concentrations lead to an OD further below zero.

Data derived from 38 healthy ambulatory laboratory workers is shown below in tabulated form. Of these, 18 had their MIC-1 genotype determined by DNA sequencing. There was a 100% agreement between the 18 subjects' DNA sequence and genotype determined by the ELISA method. A further 95 samples were analysed from healthy blood donors with 48 males and 47 females, with an age range of 20-69 and 17-71 years respectively. There were five subjects with a homozygous D6/D6 genotype, 45 with a heterozygous genotype and 45 with a homozygous H6/H6 genotype.

EXAMPLE 3

Ratiometric PCR RFLP Assay for Determination of MIC-1 Genotype

Restriction fragment length polymorphism (RFLP) assays have been a mainstay of DNA mutational analysis for many years. Some of these assays have been superseded by more sensitive, less labour intensive polymerase chain reaction (PCR) assays. In other, mutation detection, assays the two methods have been combined to detect different-DNA polymorphisms. In the case of MIC-1, the area of point mutation for the H6-D6 allele is approximately 90% GC rich. This makes it very difficult to use strategies such as competitive PCR to determine allelic, or genotypic differences. This necessitated the use of a RFLP analysis of PCR amplified DNA segments.

The RFLP assay depends on differences in DNA restriction enzyme sites conferred by differences in the DNA sequence. These sites are usually unique or give a distinct difference in the pattern of bands seen when restriction enzyme digests are separated, according to molecular weight. Typically, this is done using agarose gel DNA electrophoresis. In the region of the allelic differences in MIC-1 there are useful unique restriction sites conferred by the point mutation C to G. This necessitated a novel modification to the RFTP assay exploiting the properties of DNA agarose gel electrophoresis with ethidium bromide detection. A high agarose concentration (e.g 3%) has been employed to give better resolution for small molecular DNA bands. When irradiated with UV light, differences in ethidium bromide staining are proportional to differences in DNA concentration.

PCR primers (5p, 5'GCCGCCGCCGTCGCAGTCGGA3' SEQ ID NO: 8; 3p, 5' CAGGCGGTGCAGGCTCGTCTTGAT3' SEQ ID NO: 9) were designed to give a product such that the common AVRII sites in the D6 allele gave a major product, upon digestion, of 147 bp. In the case of the H6 allele, the extra AVRII site gave a major product of 102 bp, close to the detection limit of DNA agarose gel electrophoresis. The remaining fragment is a smaller 45 bp product that is difficult to see on agarose gel (see restriction maps in FIG. 11).

Methods:

PCR From Genomic DNA:

A standard master mix for pfu DNA polymerase (Stratagene) was made up as per the manufacturer's recommendations with 1 µl each of 10 pM 5p and 3p primers to a volume if 20 µl per reaction. 100 ng of genomic DNA from each test subject was used as template.

| PCR: | | |
| --- | --- | --- |
| Denaturation | 94° C. | 1 min |
| Annealing | 65° C. | 1 min |
| Extension | 72° C. | 2 min |

Performed for 40 cycles in MJ Research PTC-200 Peltier thermal cycler. Digest PCR products at 3° C. overnight with AVA II (New England Biolabs), as per the manufacturer's instructions.

Run on 3% agarose gel, 0.02% w/v ethidium bromide, at 80 V until separate bands were observable. Genotypes were then determined as per controls (DD, HD, HH).

Figure 12:
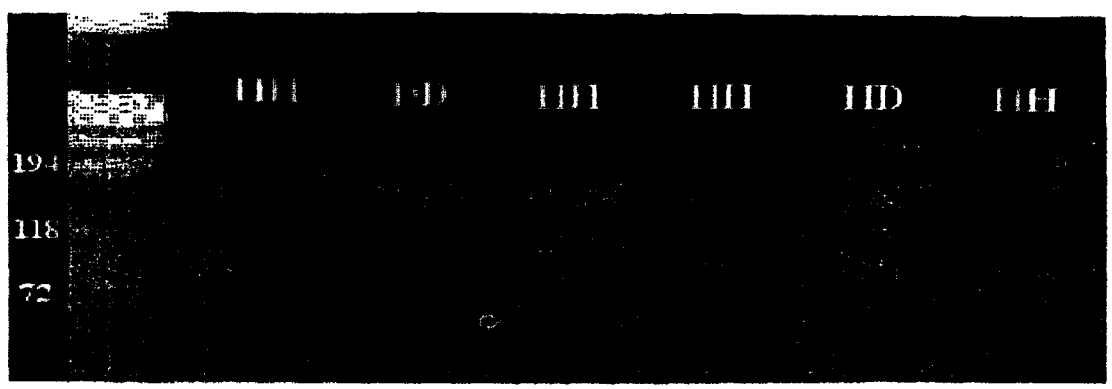

Results and Discussion:

As shown in FIG. 12, in the case of the homozysous D6/D6 allele only products of 147 base pairs are visible. The heterozygotes gave two products, 147 and 102 bp in a ratio of 3:1, while the homozygous H6/H6 gave equal amounts of the 147 and 102 bp fragment The exaggerated differences in the ratio of digestion products between the homozygous H6/H6 and the heterozygous allele is easily observable by the eye, and requires no specialised analysis. There are slight differences in intensity observed between the 147 and 102 bp products. This is due to differences in the amount of ethidium bromide intercalation. This effect further enhances differences in intensity of staining at different ratios of small products of DNA digestion. In the case of larger DNA fragments this effect is far less pronounced.

Of the 38 healthy ambulatory laboratory workers, 18 had their MIC-1 genotype determined by sequencing. Products from the above PCR were purified from agarose gel and sequenced using the manufacturer's recommended protocol for the Perkins-Elmer ABI prism DNA sequencer. Each subject had forward and reverse sequencing using the 5p and 3p primers respectively.

Results from ELISA, ratiometric PCR RFLP and DNA sequencing were tabulated (Table 1). There was 100% concordance between these methods for the 18 subjects that had DNA sequencing performed. A further 21 subjects had their genotype determined by ELISA to determine the range of 13/26 ratios for a range of concentrations of MIC-1 of various genotypes.

TABLE 1

| SPEC ID | R26 | R13 | 13/26 | MIC-1 pg/ml | Allele/ Genotype | DNA SEQUENCE |
| --- | --- | --- | --- | --- | --- | --- |
| SH | 54 | 15 | 0.3 | 270 | HD | HD |
| TL | 66 | 74 | 1.1 | 328 | HH | HH |
| AB | 50 | 12 | 0.2 | 250 | HD | HD |
| DX | 41 | 9 | 0.2 | 205 | HD | HD |
| DF | 38 | 45 | 1.2 | 192 | HH | HH |
| AC | 124 | 118 | 0.9 | 620 | HH | HH |
| JL | 36 | 6 | 0.2 | 179 | HD | HD |
| NX | 182 | 123 | 0.7 | 912 | HH | HH |
| TK | 37 | 7 | 0.2 | 185 | HD | HD |
| DJ | 48 | 44 | 0.9 | 238 | HH | HH |
| GG | 45 | <0 | <0 | 227 | DD | DD |
| JK | 83 | 21 | 0.3 | 414 | HD | HD |
| KW | 46 | 7 | 0.1 | 228 | HD | HD |
| WW | 58 | 66 | 1.1 | 291 | HH | HH |
| KS | 74 | 71 | 1 | 369 | HH | HH |
| RO | 838 | 216 | 0.3 | 4190 | HD | HD |
| DB | 33 | 38 | 1.2 | 162 | HH | HH |
| GL | 40 | 50 | 1.2 | 199 | HH | |
| KM | 80 | 98 | 1.2 | 400 | HH | |
| AsB | 719 | 384 | 0.5 | 3594 | HD | |
| NR | 112 | 90 | 0.8 | 559 | HH | |
| MS | 49 | 69 | 1.4 | 243 | HH | |
| CS | 49 | 57 | 1.2 | 243 | HH | |
| RL | 271 | 131 | 0.5 | 1355 | HD | |
| KiW | 44 | 7 | 0.2 | 218 | HD | |
| BS | 130 | 48 | 0.4 | 651 | HD | |
| MM | 65 | 21 | 0.3 | 324 | HD | |
| JZ | 66 | 27 | 0.4 | 332 | HD | |
| ML | 209 | 108 | 0.5 | 1046 | HD | |
| MN | 44 | 51 | 1.2 | 220 | HH | |

TABLE 1-continued

| SPEC ID | R26 | R13 | 13/26 | MIC-1 pg/ml | Allele/ Genotype | DNA SEQUENCE |
|---|---|---|---|---|---|---|
| CH | 39 | 8 | 0.2 | 197 | HD | |
| IS | 39 | 47 | 1.2 | 196 | HH | |
| LP | 42 | <0 | <0 | 209 | DD | |
| HL | 90 | 46 | 0.5 | 450 | DH | |
| GH | 40 | 14 | 0.3 | 201 | HD | |
| LS | 37 | 38 | 1.1 | 182 | HH | |
| DS | 503 | 521 | 1 | 2516 | HH | |
| PF | 113 | 47 | 0.4 | 565 | HD | |

EXAMPLE 4

ELISA Assays Performed with Samples from Rheumatoid Arthritis (RA) Patients

ELISA assays according to the following methods were performed on serum samples taken from an unselected population of 21 individuals with RA, and a further 9 individuals having very severe RA which had failed to respond to traditional therapies. The results are presented in Table 2 below.

Methods:

MIC-1 Sandwich ELISA:

A MIC-1 sandwich ELISA was established utilising the anti-MIC-1 mouse Mabs (13C4H3 and 26G6H6) for antigen capture and the labelled sheep polyclonal antibody (PAb 233-P) for detection. The optimum concentration of the antibodies was determined empirically then used for all subsequent studies. Ninety-six well Maxisorp ELISA plates were coated with anti MIC-1 MAb supernatant diluted 1:5 (final immunoglobin concentration was approximately 20 ng/ml) in coating buffer at 40° C. for 24 hours. Plates were then washed three times with 300 µl of wash buffer and non-specific binding was blocked with 250 µl of 1% (w/v) BSA in PBS for 2 hours at 37° C. rhMIC-1 standards, tissue culture supernatant and serum were then added to the plates (100 µl/well) and incubated for 1 hour at 37 C. The plates were washed three times followed by the addition of 100 µl/well of the sheep PAb 233B3-P diluted 1:5000 in antibody diluant and incubated for 1 hour at 37° C. The plates were then washed three times and 100 µl/well of biotinylated donkey anti-sheep IgG diluted to 1:5000 in antibody diluant was added and incubated for 1 hour at 37° C. The plates were then developed as for the direct ELISA. The concentration of hMIC-1 in the samples was determined by comparison with the rhMIC-1 standard curve.

TABLE 2

| Rheumatoid Arthritis | No. | (No.)/% of at least one D6 allele |
|---|---|---|
| Unselected RA | 21 | (1)/5% |
| Severe RA* | 9 | (4)/44% |

*RA severe enough to need experimental treatment (e.g. bone marrow transplant).

The results suggest that D6/D6 homozygote and H6/D6 heterozygote individuals have an increased predisposition to severe rheumatoid arthritis.

EXAMPLE 5

ELISA Assays Performed with Samples from Prostate Cancer Patients

ELISA assays were carried out in a manner analogous to the methods described above in Example 4 for RA, this time using serum samples taken from prostate cancer patients; 28 individuals with above average levels of prostate specific antigen (PSA), and 41 individuals with PSA levels within the normal range. The results are presented in Table 3 below.

TABLE 3

| Prostate Cancer | No. | (No.)/% of at least one D6 allele |
|---|---|---|
| PSA < 11 | 41 | (16)/39% |
| PSA > 11 | 28 | (0)/0% |

Of the samples with an elevated PSA level, no individuals were D6/D6 homozygotes or H6/D6 heterozygotes. This result suggests that the D6/D6 genotype and H6/D6 genotype may be protective for the development of prostate cancer and that this tumour is more frequently associated with other genotypes.

EXAMPLE 6

MIC-1 and Carcinoembryonic Antigen (CEA)

Figure 13:
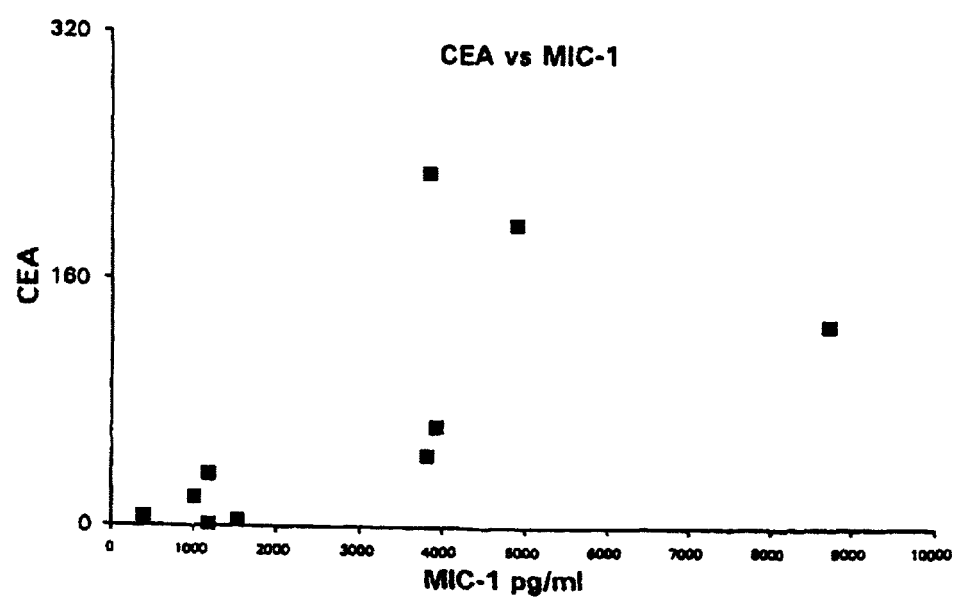
FIG. 13 shows CEA levels compared with MIC-1 in ten patients with metastatic colorectal carcinoma.

Carcinoembryonic antigen is a protein that is produced by large bowel carcinoma. It is commonly used as a measure of tumour bulk. This makes CEA a useful measure of response to various treatments. We analysed serum from ten patients with metastatic CRC and determined their MIC-1 serum level. CEA serum level was measured by standard routine laboratory analysis. There was a significant positive correlation between MIC-1 and CEA serum levels (FIG. 13). In view of the small numbers examined this is likely to be a highly significant finding.

EXAMPLE 7

MIC-1 and Colorectal Carcinoma

Epithelial malignancies form the most common group of cancers and are therefore of great scientific, medical and economic importance. Epithelial cells are subject to important regulatory influences, prominent amongst which are the TGF-β1 cytokines. They have been shown to regulate epithelial growth, cell motility and adhesion as well as being angiogenic and immunomodulatory. Multiple abnormalities of the TGF-β1 pathways have been described in breast, colonic and prostatic malignancies. These include abnormalities in their secretion, receptor expression and post-receptor pathways. In the case of the prostate, in vitro and in vivo-cell line, as well as animal studies, have shown that TGF-β1 plays a role in cell cycle "check points" and subsequent apoptosis via p53 dependant and independent pathways. Although TGF-β1 has been shown to be a negative regulatory growth factor expressed by normal prostate, throughout the course of prostate cancer the secretion may rise as a result of deregulation of the pathway. Increased serum levels of TGF-β1, measured in platelet depleted serum, are associated with a reduced survival and more rapid progression of disease. MIC-1 is a divergent member of the TGF-β1 superfamily originally identified on the basis of increased expression associated with macrophage activation. Like TGF-β1, MIC-1 is expressed in normal prostate and has been implicated in P53 dependent and independent cellular functions. Unlike TGF-β1, it is not produced by circulating vascular elements and can thus be readily measured in serum or plasma. In this example, evidence is provided for both the local expression of MIC-1 in colorectal carcinoma (CRC) and systemic release of this cytokine into blood. Results obtained also show a correlation between serum MIC-1 levels and genotypes with clinical stage and progression of CRC indicating that measurement of this cytokine has clinical and therapeutic application.

Methods

Tissue Samples:

224 consecutive individuals undergoing surgical resection of adenocarcinoma of the colon or rectum at St Vincent's Hospital, Sydney, were enrolled in this study. Individuals were excluded where pre-operative radiotherapy or chemotherapy had been administered. Individuals with inflammatory bowel disease, or with a known history of familial adenomatous polyposis (FAP) or hereditary non-polyposis coli (HNPCC) were also excluded, as were those individuals where the primary tumour was incompletely resected.

Fresh representative tissue samples (500 mg) from all tumours and paired normal colonic mucosa were immediately frozen at 70° C. In total, 224 fresh tumour specimens were assayed from 141 males and 86 females (ages 32 to 93; mean 66.6±12.4 years). Nineteen of these tumours were TNM stage I, while 22 were stage II, 111 were stage III and 72 were stage IV. Family histories of colorectal carcinoma and other malignancies were obtained by interviewing individuals or their next of kin. Attempts were made to verify all suspected diagnoses of cancer and uncertain causes of death, either by obtaining death certificates and medical records or by contacting the treating physician. The family history was used to identify those families that met either the Amsterdam or modified Amsterdam criteria for HNPCC.

Histopathological Analysis of Tumours:

For all tumours, the histopathological type, stage and size of the tumour were determined independently by a histopathologist within the Department of Anatomical Pathology, St Vincents Hospital. The tumour glade, extent of mucin production, tumour growth pattern, as well as the presence of a Crohn's-like inflammatory infiltrate, intraepithelial lymphocytes or peritumoural lymphocytes, were determined prospectively without knowledge of the mismatch repair status. Tumours in which less than 10% of cells formed glands were classified as high grade (poorly differentiated), while those containing more than 50% extracellular mucin were classified as mucinous.

The tumour growth pattern was interpreted as either infiltrative or expansile, as per previously published criteria. The extent of peritumoural and Crohn's-like lymphoid reactions was classified according to the method of Jass et al., 1996. Intraepithelial lymphocytes were identified by light microscopy on haexnatoxylin and eosin sections as cells with the morphology of lymphocytes, seen wholly within tumour epithelium. They were classified as conspicuous when more than 30 were present per 10 high power fields.

Tumour volume was estimated from reported tumour dimensions, using the formula V=p ((L+T)/4)2×D, where V=volume (ml); L=longitudinal dimension (cm); T=circumferential dimension (cm); D=depth of tumour (cm).

Analysis of Somatic Changes in p53 and K-ras:

Mutations at the first and second bases of codon 12 of the K-ras gene were detected using REMS-PCR as previously described. For the identification of accumulation of p53 within tumour cells, paraffin sections of tumour tissue were subjected to immunohistochemical analysis of p53, using the mouse anti-human p53 antibody DO7 (DAKO). A tumour was considered to show accumulation of p53 protein when more than 20% of tumour cells showed nuclear staining of moderate to high intensity, in the absence of staining in the stromal cells and normal epithelium.

In addition, the samples were examined using the MIC-1 ELISA described in Example 1 to determine the MIC-1 level and genotype. The MIC-1 serum levels and genotypes were compared to the data previously collected as outlined above, using analysis of variance, parametric and nonparametric correlates, Kaplan-Meier analysis as well as simple and logistic regression.

Results:

MIC-1 levels were stratified into normal and abnormal groups based on a normal range determined by analysis of 200 normal serum samples collected from healthy blood donors. The MIC-1 level was classified as abnormal if it was greater than 1050 pg/ml. Statistical analysis was performed using both serum and the stratified levels as stated. Where parametric testing was used the log of the serum level was used.

Subjects with higher MIC-1 serum levels had a higher Tumour TNM grade. Using analysis of variance (ANOVA), there were significant differences between grades 1 and 4 as well as grades 2 and 4 ($p<0.05$). The TNM tumour grade was stratified in to two groups, low grade (TNM grade 1-2) and high grade (TNM 3-4). To test whether the groups were significantly different, the data was analysed using the equality of variance F-test with the hypothesis that the groups were equal. The groups were different ($p<0.0001$: $F=21.01$). This difference in variance indicates that a higher MIC-1 is significantly associated with a higher grade of tumour.

Figure 14:
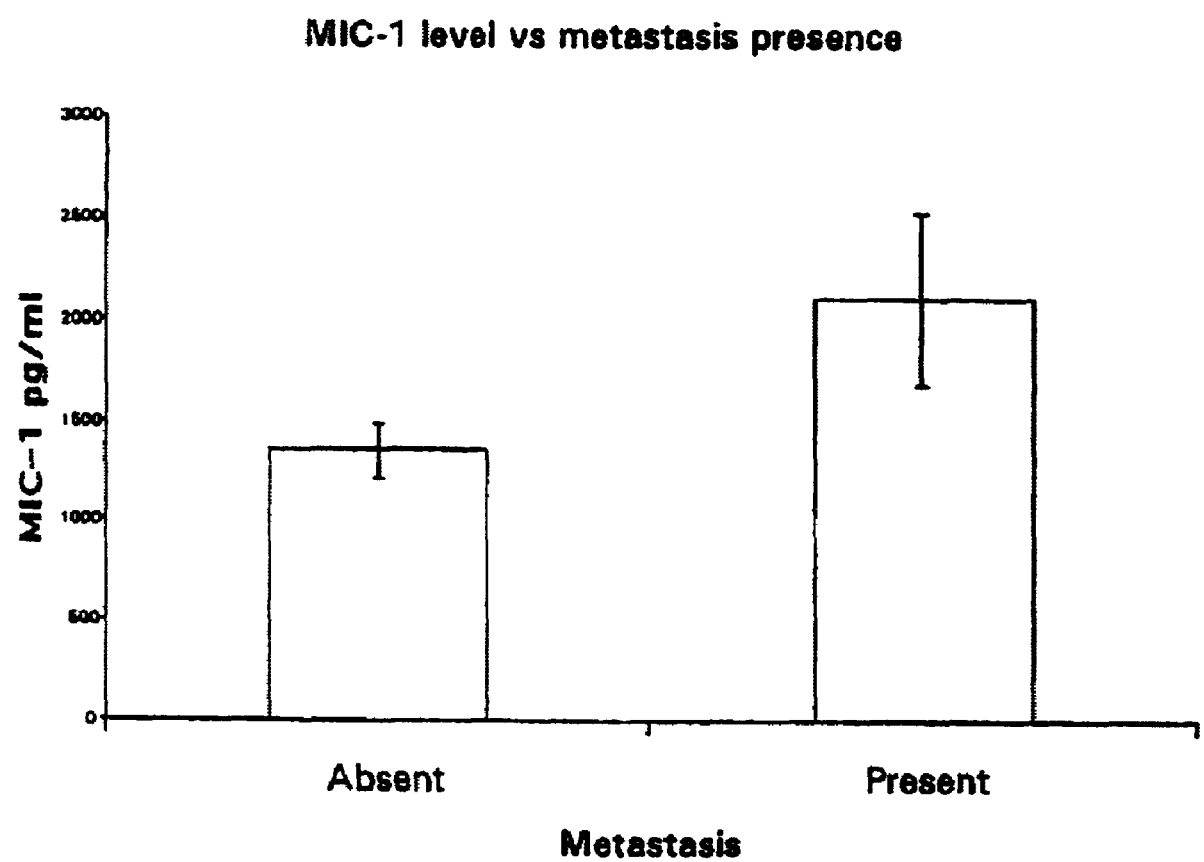
FIG. 14 shows a graph of MIC-1 levels in metastatic, compared with non-metastatic colorectal carcinoma. Error bars represent standard error.

Individuals with a high, abnormal MIC-1 levels had a greater chance of having metastatic disease, using ANOVA ($p<0.04$) (FIG. 14).

When analysing the subgroup of individuals that died of cancer there was a significant association with the homozygous H6/H6 MIC-1 genotype and a prolonged disease-free survival time. Also, heterozygous H6/D6 and homozygous D6/D6 had, respectively, shorter disease-free survival times ($p<0.02$: Logrank (Mantel-Cox)) (FIG. 15). This indicates a gene dose effect. When analysing all individuals there was a similar relationship between MIC-1 genotype and time from diagnosis to relapse. The same gene dose effect that is present in those who died of CRC is present in the whole population.

As the homozygous H6/H6 group had an increased disease-free survival, the present applicants analysed normal, compared with abnormal MIC-1 levels within this subgroup. Individuals having abnormally high levels of homozygous H6/H6 MIC-1 had a shorter time to relapse of disease, from diagnosis and initial treatment ($p<0.03$) (FIG. 16). There was no statistically significant difference in disease-free survival, between normal and abnomal serum MIC-1 levels, for subjects with the heterozygous H6/D6 or homozygous D6/D6 MIC-1 genotypes. This indicates that there are functional consequences of MIC-1 genotype on tumour behaviour.

When all individuals were analysed for the effect of MIC-1 genotype on the time to death, due to CRC, from diagnosis, there was a slight effect. Homozygous D6/D6 and heterozygous H6/D6 had an overall survival advantage compared with homozygous H6/H6. Again, a gene dose effect was discernible, but this did not reach statistical significance. As there were a small number of homozygous D6/D6 subjects they were excluded. The remaining individuals were stratified according to Dukes stage. There was an increased survival advantage with the heterozygous H6/D6 MIC-1 genotype in all groups. This reached significance in the Dukes stage D group (P<0.05) (FIG. 17). This is likely to be due to the larger overall tumour bulk in Dukes stage D which lead to higher levels of MIC-1 and therefore a larger effect.

There was also a highly significant correlation, using the correlation z-test, between MIC-1 and age (p=0.0006: Z=3.5) (FIG. 18). There was no such trend in the normal population.

There was no significant relationship between MIC-1 levels and sex, p53 phenotype, erb2, mlh1 mlh2 or tumour volume. Additionally, there was no significant difference in the MIC-1 level compared with genotype.

Discussion:

MIC-1 level correlates with the TNM stage of tumour, and the Dukes stage as well as with the presence of metastasis. This indicates that the greater the tumour bulk, the higher the MIC-1 level. The tumour volume measured was the volume of the primary tumour and was not necessarily a good representation of the entire tumour burden. When looking at the effect of genotype, there appears to be a paradox. The homozygous H6/H6 genotype is associated with a longer disease-free survival time, yet shorter overall survival. These observations could be explained by the following theory. Homozygous H6/H6 MIC-1 retards tumour growth, but also has a negative effect, in that it inhibits the immune system. After a period of time of initial tumour suppression, the tumour becomes resistant and increasingly higher levels of MIC-1 are produced. At this point the detrimental effects of the high levels of MIC-1 on the immune system become apparent, and contribute to the faster progression to death. In contrast, heterozygous H6/D6 and homozygous D6/D6 MIC-1 do not retard tumour growth, but on the positive side, they also do not suppress the immune system. So although the disease returns more quickly, there is less immune suppression. Consequently there is better tumour control and therefore longer overall survival.

This is likely to be parallel to the case of TGF-β1 in prostate cancer. As the prostate tumour develops, it is initially responsive to the negative growth effects of TGF-β1, but eventually loses its effect on the tumour due to various changes in signalling pathways. These changes lead to increased production of TGF-β1 and concomitant immunosuppression, with faster disease progression.

Elevated TGF-β1 levels have been associated with decreased overall survival in prostate cancer. TGF-β1 has been proven to decrease cell mediated immunity to prostate cancer in a dose related fashion. MIC-1 was initially isolated from a subtraction cloning library selected for macrophage activation, indicating it is likely to have effects on cellular immunity. The presence of a D allele is associated with an increased survival advantage. It is likely that this survival advantage is mediated by differential changes in cellular immune function mediated by H and D alleles. In the presence of the homozygous H6/H6 MIC-1 genotype, as the MIC-1 serum level rises there is more immunosuppression than equivalent changes in other MIC-1 genotype serum level changes. In the case of the D allele there is less immunosuppression, possibly allowing cellular immunity to keep the tumour in check, providing a survival advantage. The reason this effect is only significant in the Dukes stage D is two-fold. Firstly, there are low numbers in each group. Secondly, there are higher serum levels of MIC-1 in the Dukes stage D, hence a greater effect. These two factors contribute to the pattern seen with earlier stages of disease which don't reach statisitical significance. This is similar to the situation with TGF-β1. In the case of animals with dysfunction in one of the two TGF-β1 genes, there is an increased incidence of neoplasia.

In the case of MIC-1, with two allelic variants leading to genotypic differences in its function, mechanistic questions are raised. The point mutation in the MIC-1 molecule is in an area that is not known to be a receptor binding site for the TGF-β1 superfamily. The similar situation with TGF-β1, that the present applicants have described, is traditionally thought to be due to receptor and post-receptor abnormalities. In the case of MIC-1, the D mutation is close to the cleavage site of the mature peptide from the propeptide. Interference with the cellular processing, and, possibly secretion of MIC-1 may be an alternative explanation of functional differences between the alleles.

Clinically, the MIC-1 level and genotype may be used to stratify patients with respect to likelihood of progression to relapse and death. With reference to treatment, patients who have a D allele may benefit from homozygous H6/H6 MIC-1, but this would have to be balanced against the immunosuppressive effects of administration which may be overcome by targeted delivery.

EXAMPLE 8

Changes in MIC-1 Levels in Rheumatoid Arthritis

The present applicants also looked at two groups of individuals with rheumatoid arthritis (RA). One was an unselected group of 20 patients with RA who had had previous treatment and were presenting with a flare of disease. These individuals were treated with 1 gram of intravenous methyl prednisolone, an anti-inflammatory drug. Individuals were assessed pre-treatment and 4 and 24 hours post-treatment Serum C-reactive protein (CRP) was determined for these time points using standard laboratory techniques.

The second group consisted of 23 individuals who underwent autologous stem cell transplant for severe, active RA. These individuals had previously failed treatment with five disease modifying drugs. Stem cells were harvested after pre-treatment with granulocyte-colony stimulating factor. Individuals were then treated with high doses of cyclophosphamide, a chemotherapeutic agent. The autologous, previously harvested, stem cells, were then infused. This effectively "rescued" bone marrow function. Blood samples were taken 6 days before treatment and at 1.5 months post treatment. The CRP and tumour necrosis factor (TNF) serum levels were determined.

All individuals had a joint swollen score and a joint tender score determined, by standard methods, as well as a health assessment questionnaire (HAQ) performed. These measurements were determined for each time point.

Serum samples were analysed for MIC-1 genotype and serum level by our standard ELISA method for each time point. These results were compared with the above variables and the MIC-1 serum levels of a normal population of 100- normal blood donors.

Results:

Using an unpaired t-test MIC-1 serum levels were significantly higher in RA patients (n=43) compared with a normal population (n=100)(RA: mean=893 pg/ml: SD=614: normal: mean=406 pg/ml: SD=253 p<0.0001) (FIG. 20).

In the transplant population, MIC-1 serum levels were higher 1.5 months post-transplant compared to pre-transplant serum levels (using paired t-test analysis; p=0.021). Also, it is notable that the joint swollen and tender scores and HAQ also fell significantly (p<0.003) 1.5 months post-transplant. There were no significant changes in CRP and TNF serum levels (paired t-test). The degree of change of MIC-1 levels between pre- and 1.5 months post-transplant was positively correlated with the change in joint score at 1.5 months (p=0.006; correlation Z-test). An abnormally high MIC-1 serum level (>1050 pg/ml) post-transplant is negatively correlated with changes in TNF levels (p<0.03; Mann-Whitney-u test). The MIC-1 serum levels pre-transplant were related to TNF serum levels pre-transplant, but this just failed to reach significance (p=0.058; Kendall correlation test). There were no other significant relationships.

Taken together these trends may indicate that the MIC-1 serum level is a predictor of synovial joint dysfunction 1.5 months post transplant. The data also indicates that MIC-1 serum levels, and changes in those levels, may be related to the TNF serum level. TNF is a cytokine known to contribe to RA pathogenesis. Alternatively, this may represent increased cytokine secretion from re-constituting bone marrow.

In the unselected RA population, there was a relationship between MIC-1 serum levels and age, but this just failed to reach significance (p=0.064) using the correlation Z test.

In the transplant group homozygous H6/H6 genotype, individuals had higher TNF serum levels and higher joint swollen scores post-transplant (p<0.05; ANOVA). This was also true for the pre-transplant TNF level, but this fell just short of statistical significance (p=0.058; ANOVA).

In the unselected RA group, the HD genotype was 2 times more likely to have erosive disease (p<0.02) (FIG. 21). These individuals also had significantly lower levels of C-reactive protein (CRP) pre-treatment and at 4 and 24 hours after treatment (p<0.02; Mann-Whitney-u test). Individuals with erosive disease also had lower levels of CRP at all three time points (p<0.05; Mann-Whitney-u test) (FIGS. 22 and 23). This suggests that the genotype of MIC-1 has a functional role in determining the manifestations of RA.

Discussion:

There are clear relationships between MIC-1 genotype and erosive disease. MIC-1 genotype is also related to variations in CRP serum levels in RA. CRP is one of the major measurements of inflammatory activity in RA. Additionally, the MIC-1 serum level is significantly raised in RA compared to a normal group. Changes in MIC-1 serum levels are likely to be related to TNF serum level changes. These are MIC-1 genotype dependant. TNF is another cytokine that plays a major role in RA pathogenesis. The combined analysis of these correlations is that MIC-1 is likely to play a role in the pathogenesis of RA and that a given individual's MIC-1 genotype can predict the course of disease.

REFERENCES

Altman D. J., Schneider S. L., Thompson D. A., Cheng H. L., Tomasi T. B. (1990) A transforming growth factor beta 2-like immunosuppressive factor in amniotic fluid and localisation of the TGF-beta 2 mRNA in the pregnant uterus. J. Exp. Med. 172, 1.391-1401.

Bogdan C., Nathan C. (1993) Modulation of macrophage function by transforming growth factor beta, IL-4 and M-10. Annal. NY Acad. Sci. 685, 713-739.

Bootcov M. R., Bauskin A., Valenzuela S. M., Moore A. G., Bansal M., He C., Zhang H. P., Donnellan M., Mahler S., Pryor K., Walsh B., Nicholson R., Fairlie D. F., Por S. B., Robbins J. M., Breit S. N. (1997) MIC-1, a novel macrophage inhibitory cytokine, is a divergent member of the transforming growth factor-β superfamily cluster. Proc. Natl. Acad. Sci. USA 94, 11514-11519.

Caniggia I., Lye S. J., and Cross L C. (1997) Activin is a local regiator of human cytotrophoblast cell differentation. Endocrinology 138, 3976-3986.

Caniggia I., Grisaru-Gravnosky S., Kuliszewsly M., Post M., Lye S. J. (1999) Inhibition of TGF-β3 restores the invasive capacity of extravillous trophoblasts in pre-eclamptic pregnancies. J. Clin. Invest 103, 1641-1650.

Fairlie, W. D., Russell, P. K., Moore A. G., Zhang H -P., Brown P. K., Breit S. N. Epitope mapping of the Transforring Growth Factor-β superfamily protein, Macrophage Inhibitory Cytokine-1 (MIC-1): Identification of at least five distinct epitope specificities. Biochemistry. 2001:40:65-73.

Graham C. H., Lysiak L L, McCrae K. R., Lala P. K. (1992) Localisation of transforming growth factor at the human foetal-materal interface: role of trophoblast growth and differentiation. Biol. Reprod. 46, 561-572.

Hillier S. L., Witlin S. S., Krohn M. A., Watts D. H., Kiviat N. B., Eschenbach D. A. (1993) The relationship of amniotic fluid cytokines and preterm delivery, amniotic fluid infection, histologic chorioannionitis, and chorioamnion infection. Obstet Gynecol. 81, 941-948.

Hromas R., Hufford M., Sutton L. Xu D., Li Y., Lu L. (1997) PLAB, a novel placental bone morphogenetic protein. Biochimica et Biophysica Acta 1354, 40-44.

Jass, J. R., Ajioka, Y., Allen, J. P., Chan, Y. F., Cohen, R. J., Nixon, J. M., Radojkovic, M., Restall, A. P., Stables, S. R. and Zwi, L. J. (1996) Assessment of invasive growth pattern and lymphocytic infiltration. Histopathology 28(6), 543-548.

Laemmli U. K. (1970) Cleavage of structural proteins during the assembly of the head of bacteriophage T4. Nature London 227, 680-685.

Lang A. K., Searle R. F. (1994) The immunodomodulatory activity of human amniotic fluid can be correlated with transforming growth factor-β1 and transforming growth factor-β2 activity. Clin. Exp. Immunol. 97, 158-163.

Minarni S., Yamoto M., Nakano R. (1992) Immunohistochemical localisation of inhibin/activin subunits in human placenta. Obstet. Gynacol. 80, 410-414.

Miyazono K., Ichijo H., Heldin C -H. (1993) Transforming growth factor-β: Latent forms, binding proteins and receptors. Growth Factors 8, 11-22.

Nusing R. M., Barsig J. (1997) Inflammatory potency of activin A. Effect on prostanoid and nitric oxide formation. Adv. Exp. Med. Biol. 407, 243-248.

Opsjon S -L., Wathen N., Tingulstad S., Wiedswang G., Sundan A., Waage A., Austgulen R. (1993) Tumor necrosis factor, interleukin-1, and interleukin-6 in normal human pregnancy. Am. J. Obstet. Gynecol. 169, 397-404.

Paralkar V. M., Vail A. L., Grasser W A, Brown T A, Xu H., Vukicevic S., Ke H Z, Qi H., Owen T A, Thompson D. D. (1998) Cloning and characterisation of a novel member of the transforming growth factor-beta/bone morphogenic protein family. J. Biol. Chem. 273, 13760-13767.

Petraglia R, Woodruff T X, Botticelli G., Botticelli A., Genazzani A. R., Mayo K. E., Vale W. (1993a) Gonadotropin-releasing hormone, inhibin, and activin in human placenta: evidence for a common cellular localisation. J. Clin. Endocrinol. Metab. 74, 1184-1188.

Petraglia R, Anceschi M., Calza L., Garuti G. C., Fusaro P., Giardini L, Genazzani A K, Vale W. (1993b) Inhibin and activin in human foetal membranes: evidence for a local effect on prostaglandin release. J. Clin. Endocrinol. Metab. 77, 542-548.

Petraglia R, Sacerdote R, Cossarizani A., Angioni S., Genazzani A. D., Franceschi C., Muscettola M., Grasso G. (1991) Inhibin and activin modulate human monocyte chemotaxis and human lymphocyte interferon-gamma production. J. Clin. Endocrinol. Metab. 72, 496-502.

Petraglia R, Vaughan L, Vale W. (1989) Inhibin and activin modulate the release of GnRH, hCG, and progesterone from cultured human placental cells. Proc. And. Acad. Sci. USA 86, 5114-5117.

Qu L, Thomas K. (1992) Changes in bioactive and immunoactive inhibin levels around human labor. J. Clin. Endocrinol. Metab. 74, 1290-1295.

Roberts A. B., Sporn M. B. (1993) Physiological actions and clinincal applications of transforming growth factor-β. Growth Factors 8, 1-9.

Romero R., Mazor M., Sapulveda W, Avila C., Copeland D., Williams J. (1992) Tumour necrosis factor in preterm and term labour. Am. J. Obstet. Gynecol. 166, 1576-1587.

Wahl S. M. (1992) Transforming growth factor beta in inflammation: A cause and a cure. J Clin. Immunol. 12, 61-74.

Wallace E M, Riley S. C., Crossley L A., Ritoe S. C., Horne A., Shade M., Ellis R, Aitken D. A., Groome N. P. (1997) Dimeric inhibins in amniotic fluid, maternal serum and foetal serum in human pregnancy. J. Clin. Endocrinol. Metab. 82, 218-222.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

SEQUENCE LISTING

```
<160> NUMBER OF SEQ ID NOS: 9

<210> SEQ ID NO 1
<211> LENGTH: 308
<212> TYPE: PRT
<213> ORGANISM: Homo sapiens

<400> SEQUENCE: 1

Met Pro Gly Gln Glu Leu Arg Thr Leu Asn Gly Ser Gln Met Leu Leu
1               5                   10                  15

Val Leu Leu Val Leu Ser Trp Leu Pro His Gly Gly Ala Leu Ser Leu
                20                  25                  30

Ala Glu Ala Ser Arg Ala Ser Phe Pro Gly Pro Ser Glu Leu His Ser
            35                  40                  45

Glu Asp Ser Arg Phe Arg Glu Leu Arg Lys Arg Tyr Glu Asp Leu Leu
        50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
                100                 105                 110

Gly Leu Pro Glu Ala Ser Arg Leu His Arg Ala Leu Phe Arg Leu Ser
            115                 120                 125

Pro Thr Ala Ser Arg Ser Trp Asp Val Thr Arg Pro Leu Arg Arg Gln
        130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp Asp Cys Pro Leu Gly Pro Gly
        195                 200                 205

Arg Cys Cys Arg Leu His Thr Val Arg Ala Ser Leu Glu Asp Leu Gly
    210                 215                 220

Trp Ala Asp Trp Val Leu Ser Pro Arg Glu Val Gln Val Thr Met Cys
```

```
                    225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
                260                 265                 270

Cys Cys Val Pro Ala Ser Tyr Asn Pro Met Val Leu Ile Gln Lys Thr
                275                 280                 285

Asp Thr Gly Val Ser Leu Gln Thr Tyr Asp Asp Leu Leu Ala Lys Asp
                290                 295                 300

Cys His Cys Ile
305

<210> SEQ ID NO 2
<211> LENGTH: 308
<212> TYPE: PRT
<213> ORGANISM: Homo sapiens

<400> SEQUENCE: 2

Met Pro Gly Gln Glu Leu Arg Thr Leu Asn Gly Ser Gln Met Leu Leu
  1               5                  10                  15

Val Leu Leu Val Leu Ser Trp Leu Pro His Gly Gly Ala Leu Ser Leu
                 20                  25                  30

Ala Glu Ala Ser Arg Ala Ser Phe Pro Gly Pro Ser Glu Leu His Thr
                 35                  40                  45

Glu Asp Ser Arg Phe Arg Glu Leu Arg Lys Arg Tyr Glu Asp Leu Leu
       50                  55                  60

Thr Arg Leu Arg Ala Asn Gln Ser Trp Glu Asp Ser Asn Thr Asp Leu
 65                  70                  75                  80

Val Pro Ala Pro Ala Val Arg Ile Leu Thr Pro Glu Val Arg Leu Gly
                 85                  90                  95

Ser Gly Gly His Leu His Leu Arg Ile Ser Arg Ala Ala Leu Pro Glu
                100                 105                 110

Gly Leu Pro Glu Ala Ser Arg Leu His Arg Ala Leu Phe Arg Leu Ser
                115                 120                 125

Pro Thr Ala Ser Arg Ser Trp Asp Val Thr Arg Pro Leu Arg Arg Gln
       130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
                180                 185                 190

Arg Arg Ala Arg Ala Arg Asn Gly Asp His Cys Pro Leu Gly Pro Gly
                195                 200                 205

Arg Cys Cys Arg Leu His Thr Val Arg Ala Ser Leu Glu Asp Leu Gly
       210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
                260                 265                 270

Cys Cys Val Pro Ala Ser Tyr Asn Pro Met Val Leu Ile Gln Lys Thr
                275                 280                 285
```

```
Asp Thr Gly Val Ser Leu Gln Thr Tyr Asp Asp Leu Leu Ala Lys Asp
    290                 295                 300
Cys His Cys Ile
305

<210> SEQ ID NO 3
<211> LENGTH: 927
<212> TYPE: DNA
<213> ORGANISM: Homo sapiens

<400> SEQUENCE: 3
atgcccgggc aagaactcag gacgctgaat ggctctcaga tgctcctggt gttgctggtg      60
ctctcgtggc tgccgcatgg gggcgccctg tctctggccg aggcgagccg cgcaagtttc     120
ccgggaccct cagagttgca caccgaagac tccagattcc gagagttgcg gaaacgctac     180
gaggacctgc taaccaggct gcgggccaac cagagctggg aagattcgaa caccgacctc     240
gtcccggccc ctgcagtccg gatactcacg ccagaagtgc ggctgggatc cggcggccac     300
ctgcacctgc gtatctctcg ggccgccctt ccgaggggc tccccgaggc ctcccgcctt      360
caccgggctc tgttccggct gtccccgacg gcgtcaaggt cgtgggacgt gacacgacct     420
ctgcggcgtc agctcagcct tgcaagaccc caggcgcccg cgctgcacct gcgactgtcg     480
ccgccgccgt cgcagtcgga ccaactgctg cagaatctt cgtccgcacg gccccagctg     540
gagttgcact tgcggccgca agccgccagg gggcgccgca gagcgcgtgc gcgcaacggg     600
gaccactgtc cgctcgggcc cgggcgttgc tgccgtctgc acacggtccg cgcgtcgctg     660
gaagacctgg gctgggccga ttgggtgctg tcgccacggg aggtgcaagt gaccatgtgc     720
atcggcgcgt gcccgagcca gttccggggcg gcaaacatgc acgcgcagat caagacgagc     780
ctgcaccgcc tgaagcccga cacggtgcca gcgccctgct gcgtgcccgc cagctacaat     840
cccatggtgc tcattcaaaa gaccgacacc ggggtgtcgc tccagaccta tgatgacttg     900
ttagccaaag actgccactg catatga                                        927

<210> SEQ ID NO 4
<211> LENGTH: 927
<212> TYPE: DNA
<213> ORGANISM: Homo sapiens

<400> SEQUENCE: 4
atgcccgggc aagaactcag gacgctgaat ggctctcaga tgctcctggt gttgctggtg      60
ctctcgtggc tgccgcatgg gggcgccctg tctctggccg aggcgagccg cgcaagtttc     120
ccgggaccct cagagttgca ctccgaagac tccagattcc gagagttgcg gaaacgctac     180
gaggacctgc taaccaggct gcgggccaac cagagctggg aagattcgaa caccgacctc     240
gtcccggccc ctgcagtccg gatactcacg ccagaagtgc ggctgggatc cggcggccac     300
ctgcacctgc gtatctctcg ggccgccctt ccgaggggc tccccgaggc ctcccgcctt      360
caccgggctc tgttccggct gtccccgacg gcgtcaaggt cgtgggacgt gacacgaccg     420
ctgcggcgtc agctcagcct tgcaagaccc caggcgcccg cgctgcacct gcgactgtcg     480
ccgccgccgt cgcagtcgga ccaactgctg cagaatctt cgtccgcacg gccccagctg     540
gagttgcact tgcggccgca agccgccagg gggcgccgca gagcgcgtgc gcgcaacggg     600
gacgactgtc cgctcgggcc cgggcgttgc tgccgtctgc acacggtccg cgcgtcgctg     660
gaagacctgg gctgggccga ttgggtgctg tcgccacggg aggtgcaagt gaccatgtgc     720
atcggcgcgt gcccgagcca gttccggggcg gcaaacatgc acgcgcagat caagacgagc     780
```

```
ctgcaccgcc tgaagcccga cacggtgcca gcgccctgct gcgtgcccgc cagctacaat      840
cccatggtgc tcattcaaaa gaccgacacc ggggtgtcgc tccagaccta tgatgacttg      900
ttagccaaag actgccactg catatga                                          927

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: PCR primer

<400> SEQUENCE: 5
aggacctgct aaccaggctg cgggccaacc agagc                                  35

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: PCR primer

<400> SEQUENCE: 6
ggctaacaag tcatcatagg tctggagcga cac                                    33

<210> SEQ ID NO 7
<211> LENGTH: 9
<212> TYPE: PRT
<213> ORGANISM: Homo sapiens

<400> SEQUENCE: 7

Ala Arg Asn Gly Asp Asp Cys Pro Leu
 1               5

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 8
gccgccgccg tcgcagtcgg a                                                 21

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: PCR primer

<400> SEQUENCE: 9
caggcggtgc aggctcgtct tgat                                              24
```

The invention claimed is:

1. A method of diagnosis of colonic cancer or rectal cancer characterised by an increased level of expression of MIC-1, said method comprising;
   (i) determining the amount of MIC-1 present in a body sample taken from a human test subject,
   (ii) comparing said determined amount against the amount, or range of amounts, of MIC-1 present in equivalent body sample(s) from normal subject(s), and
   (iii) diagnosing colonic cancer or rectal cancer when the amount of MIC-1 determined in step (i) is increased compared to said amount, or range of amounts, of MIC-1 present in equivalent body sample(s) from normal subject(s) and wherein said amount determined in step (i) is greater than 1050 pg/ml;

wherein said body sample is a sample of blood serum or plasma.

2. A method of assessment of colonic cancer or rectal cancer characterised by an increased level of expression of MIC-1, said method comprising;
   (i) determining the amount of MIC-1 present in a body sample taken from a human test subject,
   (ii) comparing said determined amount against the amount, or range of amounts, present in equivalent body sample(s) from normal subject(s), and
   (iii) assessing the progression of colonic cancer or rectal cancer when the amount of MIC-1 determined in step (i) is increased compared to said amount, or range of amounts, of MIC-1 present in equivalent body sample(s) from normal subject(s) and wherein said amount determined in step (i) is greater than 1050 pg/ml;
   wherein said body sample is a sample of blood serum or plasma.

3. A method of assessment of cancer in a human subject, said method comprising a step of determining the presence of a MIC-1 D202 variant protein having the amino acid sequence shown as SEQ ID NO:1, or a mature form thereof, in a suitable sample from said human subject, wherein said determining step is achieved by immunoassay using an antibody or fragment thereof able to discriminate between said MIC-1 D202 variant protein and MIC-1 H202 protein having the amino acid sequence shown as SEQ ID NO:2, or a mature form thereof, and wherein the determined presence of said MIC-1 D202 variant protein indicates that said subject, in comparison with subjects having only said MIC-1 H202 protein, is likely to experience a relatively shorter duration to cancer reappearance following treatment, but an overall increased survival time following cancer diagnosis;
   wherein said cancer is selected from the group consisting of colonic cancer, rectal cancer and prostate cancer.

4. A method of assessing a predisposition to cancer in a human subject, said method comprising a step of determining the presence of a MIC-1 D202 variant protein having the amino acid sequence shown as SEQ ID NO:1, or a mature form thereof, in a suitable sample from said human subject, wherein said determining step is achieved by immunoassay using an antibody or fragment thereof able to discriminate between said MIC-1 D202 variant protein and MIC-1 H202 protein having the amino acid sequence shown as SEQ ID NO:2, or a mature form thereof, and wherein the determined presence of said MIC-1 D202 variant protein indicates that said subject, in comparison with subjects having only said MIC-1 H202 protein, has a decreased predisposition to cancer;
   wherein said cancer is selected from the group consisting of colonic cancer, rectal cancer and prostate cancer.

5. A method according to claim 3, wherein the cancer is prostate cancer.

6. A method according to claim 3, wherein the presence of a MIC-1 variant protein in the said sample is determined by immunoassay using antibodies or fragments thereof which specifically bind to a MIC-1 variant protein having the amino acid sequence shown as SEQ ID NO:1, or a mature form thereof.

7. A method according to claim 3, wherein said sample is whole blood, blood serum, plasma, urine or tissue biopsy.

8. A method according to claim 4, wherein the cancer is prostate cancer.

9. A method according to claim 4, wherein the presence of a MIC-1 variant protein in the said sample is determined by immunoassay using antibodies or fragments thereof which specifically bind to a MIC-1 variant protein having the amino acid sequence shown as SEQ ID NO:1, or a mature form thereof.

10. A method according to claim 4, wherein said sample is whole blood, blood serum, plasma, urine or tissue biopsy.

* * * * *